United States Patent
Cleuziat et al.

(10) Patent No.: US 6,218,151 B1
(45) Date of Patent: Apr. 17, 2001

(54) METHOD FOR NUCLEIC ACID AMPLIFICATION BY TRANSCRIPTION USING DISPLACEMENT, AND REAGENTS AND KIT THEREFOR

(75) Inventors: Philippe Cleuziat, Lyons; Francoise Guillou-Bonnici; Francois Mallet, both of Villeurbanne; Pierre Levasseur, Lyons, all of (FR)

(73) Assignee: Bio Merieux, Marcy l'Etoile (FR)

(*) Notice: Subject to any disclaimer, the term of this patent is extended or adjusted under 35 U.S.C. 154(b) by 0 days.

(21) Appl. No.: 09/056,953

(22) Filed: Apr. 8, 1998

Related U.S. Application Data

(63) Continuation of application No. 08/406,849, filed on Apr. 24, 1995, now Pat. No. 5,849,547.

(30) Foreign Application Priority Data

Jul. 26, 1993 (FR) .................................................. 93 09187

(51) Int. Cl.⁷ .............................. C12P 19/34; C12Q 1/68
(52) U.S. Cl. ............................. 435/91.2; 435/91.2; 435/6
(58) Field of Search ............................. 435/6, 91.2, 91.1, 435/91.21

(56) References Cited

U.S. PATENT DOCUMENTS

| | | |
|---|---|---|
| 5,169,766 | 12/1992 | Schuster et al. . |
| 5,348,853 * | 9/1994 | Wang et al. .......................... 435/6 |
| 5,409,818 | 4/1995 | Davey et al. . |
| 5,422,252 | 6/1995 | Walker et al. . |
| 5,437,990 | 8/1995 | Burg et al. . |
| 5,480,784 | 1/1996 | Kacian et al. . |
| 5,578,458 * | 11/1996 | Caskey et al. ....................... 435/6 |
| 5,599,696 * | 2/1997 | Mueller et al. .................. 435/91.2 |

FOREIGN PATENT DOCUMENTS

| | | |
|---|---|---|
| 0 501 395 | 9/1992 | (EP) . |
| 0 543 612 | 5/1993 | (EP) . |
| WO-A 93 05184 | 3/1993 | (WO) . |
| WO 97/00330 | 1/1997 | (WO) . |

OTHER PUBLICATIONS

M. Iyer et al., "Accelerated Hybridization of Oligonucleotides to Duplex DNA", *Journal of Biological Chemistry*, vol. 270, No. 24, pp. 14712–14717, (1995).

* cited by examiner

Primary Examiner—Lisa B. Arthur
(74) Attorney, Agent, or Firm—Oliff & Berridge, PLC

(57) ABSTRACT

The extension of primers capable of hybridizing to the nucleic acid of interest results in a process for generating single-stranded polynucleotides. The process includes contacting the nucleic acid of interest under conditions allowing extension of the primers with a first primer and a second primer capable of hybridizing to a first region and a second region, respectively, of the nucleic acid, wherein the second region overlaps with the first region.

4 Claims, 19 Drawing Sheets

LEGEND:
- COMPLETE AMPLIFICATION SYSTEM
- AMPLIFICATION SYSTEM WITHOUT DISPLACEMENT PRIMER F220
- AMPLIFICATION SYSTEM WITHOUT REVERSE TRANSCRIPTASE (TRANSCRIPTION)

LEGEND:
- 10 EXP 9 COPIES / TEST
- 10 EXP 8 COPIES / TEST

LEGEND: QUANTITY OF T7/T3 RNA POLYMERASE PER TEST
- ■ 50 U/50 U
- ▨ 25 U/50 U
- ▥ 12.5 U/50 U
- ▧ 6.25 U/50 U
- ☐ 0 U/50 U

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
       (A) LENGTH: 861 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:1:

```
ATGAGTATTC AACATTTCCG TGTCGCCCTT ATTCCCTTTT TTGCGGCATT TTGCCTTCCT     60
GTTTTTGCTC ACCCAGAAAC GCTGGTGAAA GTAAAAGATG CTGAAGATCA GTTGGGTGCA    120
CGAGTGGGTT ACATCGAACT GGATCTCAAC AGCGGTAAGA TCCTTGAGAG TTTTCGCCCC    180
GAAGAACGTT TTCCAATGAT GAGCACTTTT AAAGTTCTGC TATGTGGCGC GGTATTATCC    240
CGTGTTGACG CCGGGCAAGA GCAACTCGGT CGCCGCATAC ACTATTCTCA GAATGACTTG    300
GTTGAGTACT CACCAGTCAC AGAAAAGCAT CTTACGGATG GCATGACAGT AAGAGAATTA    360
TGCAGTGCTG CCATAACCAT GAGTGATAAC ACTGCGGCCA ACTTACTTCT GACAACGATC    420
GGAGGACCGA AGGAGCTAAC CGCTTTTTTG CACAACATGG GGGATCATGT AACTCGCCTT    480
GATCGTTGGG AACCGGAGCT GAATGAAGCC ATACCAAACG ACGAGCGTGA CACCACGATG    540
CCTGCAGCAA TGGCAACAAC GTTGCGCAAA CTATTAACTG GCGAACTACT TACTCTAGCT    600
TCCCGGCAAC AATTAATAGA CTGGATGGAG GCGGATAAAG TTGCAGGACC ACTTCTGCGC    660
TCGGCCCTTC CGGCTGGCTG GTTTATTGCT GATAAATCTG GAGCCGGTGA GCGTGGGTCT    720
CGCGGTATCA TTGCAGCACT GGGGCCAGAT GGTAAGCCCT CCCGTATCGT AGTTATCTAC    780
ACGACGGGGA GTCAGGCAAC TATGGATGAA CGAAATAGAC AGATCGCTGA GATAGGTGCC    840
TCACTGATTA AGCATTGGTA A                                              861
```

(2) INFORMATION FOR SEQ ID NO:2:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:2:

```
AATTCTAATA CGACTCACTA TAGGGAGACC CCGAAGAACG TTTTC                     45
```

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:3:

CTCCTTCGGT CCTCCGATC                                                      19

(2) INFORMATION FOR SEQ ID NO:4:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:4:

AGTTGGGTGC ACGAGTGGG                                                      19

(2) INFORMATION FOR SEQ ID NO:5:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:5:

CACTCATGGT TATGGCA                                                        17

(2) INFORMATION FOR SEQ ID NO:6:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:6:

AATTCTAATA CGACTCACTA TAGGGAGATT ACCAATGCTT AATCA                         45

(2) INFORMATION FOR SEQ ID NO:7:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:7:

ATGAGTATTC AACATTTC                                                       18

(2) INFORMATION FOR SEQ ID NO:8:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "DNA"

(xi) SEQUENCE DESCRIPTION: SEQ ID NO:8:

TCTAATCCTG TTTGCTCCCC AGTAATTTAA TACGACTCAC TATAGAAAGA ACCAGTCACA   60

GAAAGGCAT   69

(2) INFORMATION FOR SEQ ID NO:9:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

TCTAATCCTG TTTGCTCCCC AGTAATTTAA TACGACTCAC TATAGAAAGA ACGATCAAGG   60

CGAGTTACA   69

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

TCTAATCCTG TTTGCTCCCC   20

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

TGCCATAACC ATGAGGT   17

(2) INFORMATION FOR SEQ ID NO:12:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

TCTAATCCTG TTTGCTCCCC AGTAATTTAA TACGACTCAC TATAGAAAGA GGATGGCATG   60

ACAGTA   66

(2) INFORMATION FOR SEQ ID NO:13:

(i) SEQUENCE CHARACTERISTICS:

(A) LENGTH: 67 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

TCTAATCCTG TTTGCTCCCC AGTAATTTAA TACGACTCAC TATAGAAAGA GTTGGCCGCA        60

GTGTTAT        67

(2) INFORMATION FOR SEQ ID NO:14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

AGAGAATTAT GCAGTGC        17

(2) INFORMATION FOR SEQ ID NO:15:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

ATAACACTGC GGCCAAC        17

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

TAATACGACT CACTATAG        18

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

GCACTGCATA ATTCTCT        17

(2) INFORMATION FOR SEQ ID NO:18:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

```
TCTAATCCTG TTTGCTCCCC AGTAATTAAT TAACCCTCAC TAAAGGGAAC GGATGGCATG      60

ACAGTA                                                                66
```

METHOD FOR NUCLEIC ACID AMPLIFICATION BY TRANSCRIPTION USING DISPLACEMENT, AND REAGENTS AND KIT THEREFOR

This application is a continuation of application Ser. No. 08/406,849, filed Apr. 24, 1995, now U.S. Pat. No. 5,849,547, which is the national stage application of PCT/FR94/000934, filed Jul. 26, 1994.

FIELD OF THE INVENTION

The present invention refers to the methods, reagents and kits for the amplification of target nucleic acid sequences. In particular, the present invention consists in a method for the amplification of nucleic acids by transcription, using displacement, and the detection of the amplification products obtained by this reaction.

DESCRIPTION OF THE RELATED ARTS

It is often necessary, in technologies relating to nucleic acids and to genetic material, to determine if a gene, a gene portion or a nucleotide sequence is present in a living organism, a cellular extract of this organism or a biological sample. Since any gene or gene portion is a specific sequence of nucleotide bases forming all or part of a nucleotide molecule, it is possible to directly search for the presence of a specific nucleotide sequence in a sample containing polynucleotides.

The usefulness of the search for specific nucleotide sequences is immense, especially for the detection of pathogenic organisms, the determination of the presence of alleles, the detection of the presence of lesions in a host genome and the detection of the presence of a specific mRNA or of the modification of a cellular host. Genetic diseases such as Huntington's disease, Duchenne's myopathy, phenylketonuria and β-thalassemia can be diagnosed by analysing DNA from the individual. Furthermore, the diagnosis or the identification of viruses, viroids, bacteria, fungi, protozoa or some other form of plant or animal life can be carried out by hybridization experiments with nucleic probes.

Various types of methods for the detection of nucleic acids are described in the literature. These methods, and particularly those which require the detection of polynucleotides, are based on the purine-pyrimidine pairing properties of the complementary strands of nucleic acids in the DNA—DNA, DNA-RNA and RNA—RNA complexes. This pairing process occurs by the establishment of hydrogen bonds between the adenosine-thymine (A—T) and guanosine-cytosine (G—C). bases of the double-stranded DNA; adenosine-uracil (A—U) base pairs can also be formed by hydrogen bonding in the DNA-RNA or RNA—RNA duplexes. The pairing of nucleic acid strands for the determination of the presence or of the absence of a given nucleic acid molecule is commonly called "nucleic acid hybridization" or simply "hybridization".

In the few examples mentioned above, after identifying a sequence specific for an organism or for a disease, it is advisable to extract the nucleic acids from a sample, and to determine if this sequence is present. Numerous detection methods have been developed for this purpose.

While it is vital that one or more sequences specific for a disease or for an organism are identified, the nature of these sequences and the manner in which they were identified is of no particular importance for the implementation of the present invention. The most direct method for detecting the presence of a target sequence in a nucleic acid sample is to obtain a "probe" whose sequence is sufficiently complementary to a portion of the target nucleic acid to hybridize to the latter. The probe thus synthesized can be applied in a sample containing nucleic acids, and if the target sequence is present, the probe will hybridize in order to form a reaction product. In the absence of target sequence and by avoiding any non-specific hybridization phenomenon, no reaction product will be formed. If the synthesized probe is coupled to a detectable marker, the reaction product can be detected by measuring the quantity of marker present. Southern blotting (Southern E. M., *J. Mol. Biol.,* 98, 503 (1975)) or sandwich hybridization (Dunn A. R., Hassel J. A., *Cell,* 12, 23 (1977)) constitute examples where these methods are used.

The principal difficulty of this approach is, however, that it is not directly applicable to cases where the copy number of the target sequence present in a sample is low (that is to say less than $10^7$). Under these conditions, it is difficult to differentiate a significant signal, that is to say greater than the reaction background noise (that is to say to differentiate the specific binding of a probe onto its target sequence for the non-specific binding between the probe and a sequence different from the target sequence). One of the solutions to this problem consists of increasing the detection signal by an additional reaction. Consequently, various methods have been described in order to increase the power of detection of these hybridization techniques. These so-called "amplification" methods can be used at various stages in a method of detection by nucleic probes. These stages can be classified into three categories: the amplification of target, of probe or of signal. The articles by Lewis (1992. *Genetic Engineering News* 12:1–9) on the one hand, and by Abramson and Myers (1993. *Curr. Opin. Biotechnol.* 4:41–47) on the other hand, constitute good general reviews of these methods.

The amplification of target consists of multiplying, in specific manner, a nucleic acid fragment present in a sample. It makes it possible to considerably increase the copy number of a target nucleic sequence to be detected.

The most widely known method is the Polymerase Chain Reaction (called PCR), a target amplification technique which is based on the repetition of cycles of DNA synthesis in vitro by extension of nucleotide primers hybridized with the target sequence (Saiki et al., 1985. *Science* 230:1350–1354; U.S. Pat. Nos. 4,683,195, 4,683,202 and 4,800,159; European Patent No. 0,201,184). Briefly, two nucleotide primers each complementary to a sequence of one of the two strands of the target DNA are synthesized. Deoxyribonucleoside triphosphates are added in excess to the reaction medium in the presence of a thermostable DNA-dependent DNA polymerase (Taq polymerase). If the target DNA is present in the sample, the primers hybridize with their specific sites and the polymerase extends the 3' end of these primers by adding successively nucleotides complementary to the target. By carrying out successive cycles of rise and fall in temperature, the extended primers separate from the target and can, like the original target, bind the nucleotide primers in excess. By repeating the process (from 20 to 40 times, an exponential accumulation of the target sequence between the two primers is obtained.

Another method using temperature cycles is described in European Patent No. 0,320,308 and is called Ligase Chain Reaction (termed LCR). Two adjacent oligonucleotide probes, as well as two others which are complementary to them are added to the reaction medium in excess, in the presence of a DNA ligase. In the presence of the target DNA, each oligonucleotide hybridizes with its complementary sequence and the ligase can link the two adjacently hybridized probes. By a succession of temperature cycles, like in PCR, and by the use of a thermostable ligase (Barany, 1991. Proc. Natl. Acad. Sci. USA 88:189–193), the linked probes separate from the target and can in turn serve as target sequence for the probes in excess.

The Repair Chain Reaction method (termed RCR) is an amplification method similar to LCR (Patent Application No. WO 90/01069). It is a hybrid method between PCR and LCR. It uses two oligonucleotide probes complementary to the target and two primers in excess in the reaction medium, in the presence of a thermostable DNA ligase and a thermostable DNA polymerase. In the presence of target DNA, the oligonucleotides hybridize with their target sequence and a gap of a few bases separates the end of each primer from the adjacent oligonucleotide probe. The polymerase fills this gap and also makes possible the action of the ligase which links the extended primer to the adjacent probe, thus mimicking the natural processes of DNA repair. By a succession of temperature cycles, as in PCR and LCR, the extended primers linked to the oligonucleotide probes can in turn serve as target for the primers and the probes in excess.

Other target amplification methods exist which are based on the amplification of transcripts (termed TAS). TAS, which is described in U.S. patent application Ser. No. WO 88/10315, consists of the repetition of a cycle with three stages. The first stage makes it possible to synthesize a cDNA from RNA in the presence of reverse transcriptase and a "hybrid" deoxynucleotide primer containing a specific sequence of phage RNA polymerase promoter. Following the thermal denaturation of the RNA/cDNA heteroduplex, the single-stranded cDNA is replicated by reverse transcriptase in the presence of an anti-sense oligonucleotide primer. The DNA homoduplex thus obtained during this second stage contains a double-stranded promoter to which a phage DNA-dependent RNA polymerase can bind. The third stage then consists of transcribing RNA molecules (from 30 to 1000 per template) which will again be able to serve as template for the synthesis of cDNA and thereby to continue the amplification cycle (Davis et al., 1990. J. Infect. Dis. 162:13–20).

There are various methods derived from TAS, including Self-Sustained Sequence Replication (termed 3SR), which is described in U.S. patent application Ser. No. WO 90/06995 and European Patent No. 0,373,960, Nucleic Acid Sequence-Based Amplification (termed NASBA) which is described in Patent Application WO 91/02818 and European Patent No. 0,329,822 and Single Primer Sequence Replication (termed SPSR) which is described in U.S. Pat. No. 5,194,370. These methods have in common the combination of three enzymatic activities: RNA- and DNA-dependent DNA polymerase (reverse transcriptase), ribonuclease H (RNase H; Escherichia coli enzyme and/or enzymatic activity associated with reverse transcriptase), and DNA-dependent RNA polymerase (T7 bacteriophage RNA polymerase). These methods are based on the same principle and are carried out at a fixed temperature (from 37 to 45° C.), according to a continuous process of reverse transcription and transcription reactions in order to replicate an RNA target via cDNA. As in the case of TAS, an RNA polymerase (T7 phage) binding site is introduced into the cDNA by the primer used for the reverse transcription stage. However, the denaturation of the RNA/cDNA heteroduplex is carried out isothermally by specific hydrolysis of the RNA of this heteroduplex by RNase H activity. The free cDNA is then replicated from a second oligonucleotide primer by reverse transcriptase. The DNA/DNA homoduplex is transcribed into RNA by T7 RNA polymerase and this RNA can again serve as template for the next cycle.

Another method, Ligation Activated Transcription (termed LAT) described in U.S. Pat. No. 5,194,370, uses the same enzymatic activities as 3SR, SPSR and NASBA and operates on the same cycle. It differs however by the mode of installation of a promoter sequence which, in this case, is introduced at the end of the cDNA by ligation of a stem-loop structure containing the promoter, in the presence of a DNA ligase.

Other target amplification methods are currently described. The Strand Displacement Amplification method (termed SDA), described in European Patent No. 0,497,272, allows an isothermal multiplication (37° C.) of a target DNA sequence with the aid of an appropriate restriction enzyme and a DNA-dependent DNA polymerase lacking exonuclease activity (Walker et al., 1992. Proc. Natl. Acad. Sci. USA 89:392–396). It is based on the hybridization of oligonucleotide primers containing a sequence for recognition of a restriction enzyme at their 5' end. These primers are extended on the target by DNA polymerase in the presence of at least one modified nucleotide (5'[α-thio]dNTP). The digestion of the DNA by restriction endonuclease causes the cleavage of the strand corresponding to the primer, leaving intact the modified complementary strand. DNA polymerase can carry out the extension of the primer thus generated and liberates a DNA strand into the reaction medium using the strand displacement property of DNA polymerase. This liberated strand can then bind a primer containing a restriction enzyme binding sequence and the cycle can then start again. Moreover, a method of preparing nucleic acids having defined ends and capable of subsequently serving in an amplification method, especially the above-mentioned SDA, is described in European Patent Application 543 612. It should however be noted that this method of preparation, by itself, cannot in any case give rise to an isothermal amplification cycle. A method similar to SDA, using an exonuclease activity instead of endonuclease activity, called exonuclease-mediated strand displacement amplification, is described in European Patent No. 0,500,224.

For all the methods described above, a variety of detection methods can be used. One of them consists of detecting the reaction products having a defined size by electrophoretic separation. The methods vary according to the separation method, which may involve gel separation, binding to various solid phases (beads, microtitre plate, latex, magnetic particles). Another method uses the labelling of a detection probe with a radioisotope such as $^{32}P$, for example, followed by the detection of the radioactivity denoted by the reaction products in combination or otherwise with an electrophoresis. Another method consists of chemically modifying an oligonucleotide primer by adding to it a ligand (biotin or digoxigenin for example), an enzyme (alkaline phosphatase, peroxidase, β-galactosidase for example), a fluorescent marker (phycobiliprotein, fluorescein, rhodamine for example), a luminescent marker (an acridinium ester for example) or a combination of these modifications. Another method consists of developing a detection nucleotide primer which will hybridize with the reaction product of amplification and will be extended by a polymerase in the presence of ribonucleoside triphosphates (this primer can in this case also be modified as described above). All these methods can be adapted on a solid phase as well as in solution (homogeneous phase).

However, all the amplification techniques previously presented possess at least one major limitation. They make it possible to obtain an amplification product only from a single type of target nucleic acid: RNA or DNA. In some cases such as PCR, LCR or RCR, the most limiting factor is the need to carry out numerous temperature cycles in order to separate the reaction products from the target. This limits the choice of enzymes which can be used to thermostable enzymes. Furthermore, the carrying out of such successive temperature cycles constitutes a disadvantage for automating these techniques. Another disadvantage of certain amplification techniques is the limitation of the size of the amplification reaction product. Techniques such as RCR or LCR make it possible to amplify only the sequence of the target corresponding to the nucleotide primers and probes used in the amplification process. The non-specific background noise (that is to say in the absence of the target) is also a serious disadvantage of certain techniques such as LCR; in the case of LCR, ligation of the ends of the free oligonucleotides in excess occurs in the absence of the target. Other methods such as SDA are limited in the type of target sequence to be amplified since this sequence should not contain a restriction site corresponding to the endonuclease used in the process, it is therefore essential to know, if not the nucleic sequence of the fragment to be amplified, at least the restriction map of the said fragment. In addition, this limitation is increased by the fact that the choice of restriction endonucleases is restricted to those having the ability to cleave a hemiphosphorothioate recognition site (that is to say comprising a DNA strand of the duplex with at least one modified nucleotide of the phosphorothioate type), and, from a more general point of view, the sites containing modified nucleotides. In addition to the limitations in the choice of the modified nucleotide, which are due to chemical synthesis, the amplification process is also limited by its yield since it is known that the Km of the polymerases for the modified nucleotides is greater than that for the natural nucleotides for the polymerases, hence a lower efficiency of enzymatic incorporation of the modified nucleotides into the target to be amplified. Another major disadvantage of certain amplification techniques lies in the high number of enzymatic activities involved in the amplification process. The methods derived from TAS, such as 3SR or NASBA, require at least four enzymatic activities (DNA-dependent DNA polymerase, RNA-dependent DNA polymerase, DNA-dependent RNA polymerase, RNase H), or even five in the case of LAT (DNA ligase in addition). It is consequently very difficult to make these techniques efficient because of the difficulty of obtaining reaction conditions simultaneously satisfying these four or five enzymatic activities. Furthermore, these transcriptional techniques allow amplification only from RNA target molecules, but not DNA. Finally, while various amplification techniques use nuclease activities (exonuclease, endonuclease, RNase) as means for separating strands of nucleic acids (European Patent No. 0,500,224), their use is nevertheless damaging because of the possibility of degradation of the target or of the reaction product by unwanted nuclease activities which are sometimes present in preparations of such nuclease activities. Furthermore, in the case of transcriptional techniques, the use of RNases leads to a partial degradation of the amplified material and therefore impairs the yield and the sensitivity of the technique. Furthermore, the action of RNase should be rigorously measured so as to maintain an equilibrium with the action of the various enzymes involved. In the light of these numerous limitations, other amplification methods which are alternatives to these existing methods are desirable.

SUMMARY OF THE INVENTION

The present invention provides a method of amplifying a target nucleic acid sequence (RNA and/or DNA) of any sequence (as well as its complementary sequence) in a sample, by transcription reaction using displacement. The method includes various stages allowing the detection of a target nucleic acid sequence in a sample. The method may comprise especially: 1) the extraction of the nucleic acids from a biological sample capable of containing the desired target sequence, 2) the denaturation of the target sequence, that is to say the production of single-stranded fragments if the target is a duplex, 3) the addition of a reaction mixture containing (a) an enzyme or a mixture of enzymes having DNA- and RNA-dependent DNA polymerase activity and a strand-displacement activity, (b) an RNA polymerase, (c) an oligonucleotide primer successively composed (from 5' to 3') of an arbitrary optional sequence of at least 5 nucleotides, of a sequence containing all or part of a promoter sequence for an RNA polymerase, and then a sequence complementary to the 3' end of a target nucleic acid fragment, and/or (d) an optional oligonucleotide primer containing at its 3' end all or part of the arbitrary sequence of the primer defined in 3c, and/or (e) an optional nucleotide primer possessing at its 3' end all or part of the primer defined in 3c, whose 3' end hybridizes downstream (3') of the primer defined in 3d and capable of comprising at least the 5' part of a sense sequence of the promoter but not comprising the 3' end of the primer defined in 3c, (f) the deoxyribonucleoside triphosphates and ribonucleoside triphosphates, (g) a buffer appropriate for the function of the enzymatic activities and 4) the carrying out of an incubation for a minimum period in order to generate the reaction products.

The invention also extends to the methods of separating and/or detecting the reaction products by various methods, including those described above. The separation methods comprise, inter alia, magnetic separation, capture on a solid support, on a membrane, on a filter or on a polymer. In each method, a capture residue can be attached to a magnetic bead, to a membrane, to a filter or to a polymer. The beads, the membrane, the solid support, the filter or the polymer can then be tested for the presence or the absence of the reaction product of the amplification method. The capture residues can be for example a nucleic acid sequence complementary to the amplification reaction product, proteins or antibodies directed against a ligand or a haptene incorporated into one of the primers used, or into the reaction product. The separation system may be or may not be coupled to the detection system.

The detection systems which are useful for the practical implementation of the invention comprise homogeneous systems (that is to say which do not require a separation system) and, on the other hand, heterogeneous systems. In each system, one or more detectable markers are used and the reaction or the emission of the detection system is measured, preferably by automated means. Examples of homogeneous detection systems comprise the transfer of fluorescence energy, protection by hybridization (luminescence of acridinium), polarization of fluorescence and immunological detection of a cloned enzyme donor. Examples of heterogeneous systems comprise enzymatic markers (peroxidase, phosphatase, β-galactosidase), fluorescent markers (enzymatic markers, rhodamine, fluorescein), chemiluminescence and bioluminescence. In these detection systems, the detectable markers can be conjugated directly or indirectly to a capture residue, or the amplification reaction products can be generated in the presence of a protein or of an antibody which can be recognized by a ligand or a haptene for the latter.

The subject of the invention is also a method for the indirect detection of a molecule of interest in which the polynucleotide which is a marker coupled to the molecule of interest is amplified. The amplification products of the marker polynucleotide can themselves be detected directly by incorporation during their synthesis of modified nucleotides such as labelled with [$^{32}$P] or with [$^{3}$H] or can also be detected indirectly according to the methods described above.

The invention also relates to the methods for generating amplification products which can be used as probe, or which can be used as template for the determination of its nucleotide sequence. The amplified products can be separated from the enzymes used for the amplification (DNA polymerase and RNA polymerase), so as to be used in subsequent processes involving other enzymatic reactions, other amplification systems, sequencing methods or methods of synthesizing nucleic acids, to mention just a few examples.

BRIEF DESCRIPTION OF THE DRAWINGS

The subject of the invention is also a kit for the detection of a target nucleic acid which may be present in a sample allowing the implementation of the amplification method described above.

The invention will now be described in greater detail with reference, where appropriate, to the accompanying drawings in which.

Figure 1:
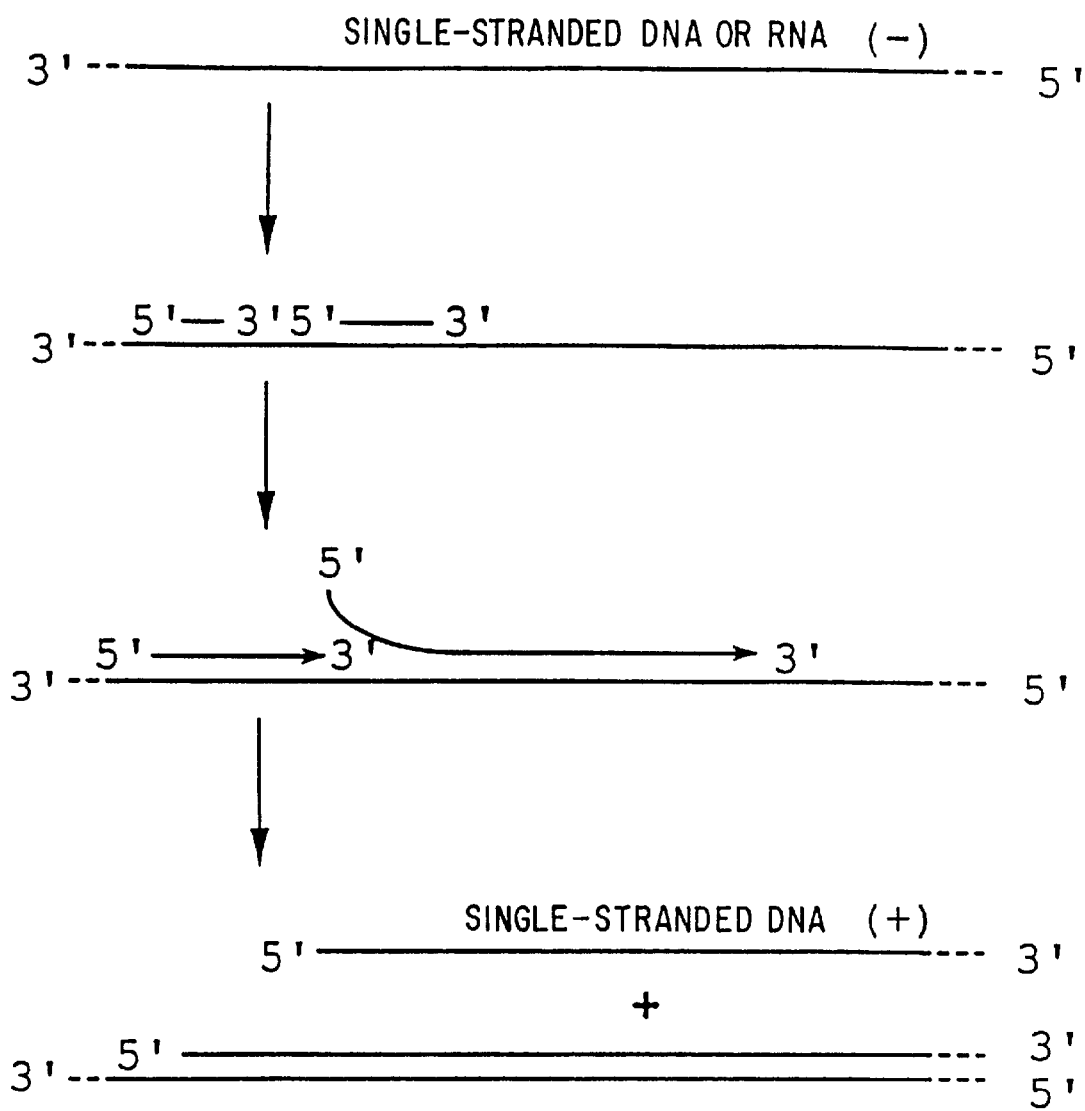
FIG. 1 describes the principle of separating a nucleic acid strand from a duplex using strand displacement properties of certain polymerases.

According to the invention, the method of amplifying a sequence of a target nucleic acid, the said sequence comprising, from its 5' end, in the 5'-3' direction, an upstream sequence having at least 5 nucleotides and from its 3' end in the 3'-5' direction, a downstream sequence having at least 5 nucleotides, comprises the steps consisting:

of obtaining a polynucleotide comprising a first segment corresponding to the sequence to be amplified and comprising, in addition, at least a second segment chosen from segments comprising the sense sequence or the antisense sequence of an RNA polymerase promoter or at least a portion of the said sense or antisense sequence, it being understood that such a second segment comprising the said sense sequence or a portion thereof is situated upstream of the 5' end of the said first segment, and that such a second segment comprising the said antisense sequence or a portion thereof is situated downstream of the 3' end of the said first segment, and of bringing the said polynucleotide, in the presence of a system having an RNA polymerase activity, an RNA-dependent DNA polymerase activity, a DNA-dependent DNA polymerase activity and a strand displacement activity, under conditions allowing the function of the said activities, and in the presence of an excess of deoxyribonucleoside triphosphates and ribonucleoside triphosphates, into contact with a set of primers, which are present in excess, comprising:

a) a first primer comprising successively from its 5' end towards its 3' end:
a first polynucleotide segment of arbitrary sequence, and whose presence as constituent of the first primer is optional, the said first segment, when it is present, comprising at least 5 nucleotides,
a second segment comprising all or part of a sense sequence of a promoter for an RNA polymerase, or comprising at least a portion of the said sense sequence including its 3'-terminal portion,
and a third segment having the same length as the said upstream sequence and being either homologous to the said upstream sequence, or capable of hybridizing with the said upstream sequence, and/or b) a second primer comprising successively, from its 5' end towards its 3' end:
a first optional segment defined like the first segment of the first primer, but not necessarily identical to it,
a second segment defined like the second segment of the first primer, but not necessarily identical to it,
and a third segment having the same length as the said downstream sequence and being either homologous to the said downstream sequence, or capable of hybridizing with the said downstream sequence, it being understood that the third segment of one of the first and second primers is homologous to one of the upstream or downstream sequences of the said sequence to be amplified, whereas the third segment of the other primer is capable of hybridizing with the other downstream or upstream sequence, and/or c) a third and/or a fourth optional primer comprising:
either a sequence homologous to the second segment of the first primer and of the second primer respectively, and containing at least a portion of a sense sequence of the said RNA polymerase promoter including its 5'-terminal portion, or a sequence homologous to a portion of the first segment of the first and second primer respectively, but not comprising their 5' portion, and/or d) a fifth and/or a sixth optional primer comprising:
either a sequence homologous to a portion of the third and of the fourth primers respectively, the said portion not comprising the 3'-terminal nucleotide of the said third or fourth primer,
or a sequence homologous to at least a portion of the said first segment of the first and of the second primers respectively.

According to a specific embodiment of the amplification method according to the invention, the latter comprises the steps consisting:

of obtaining a polynucleotide comprising a first segment corresponding to the sequence to be amplified and comprising, in addition, at least a second segment chosen from segments comprising the sense sequence or the antisense sequence of an RNA polymerase promoter or at least a portion of the said sense or antisense sequence, it being understood that such a second segment comprising the said sense sequence or a portion thereof is situated upstream of the 5' end of the said first segment, and that such a second segment comprising the said antisense sequence or a portion thereof is situated downstream of the 3' end of the said first segment, and of bringing the said polynucleotide, in the presence of a system having an RNA polymerase activity, an RNA-dependent DNA polymerase activity, a DNA-dependent DNA polymerase activity and a strand displacement activity, under conditions allowing the function of the said activities, and in the presence of an excess of deoxyribonucleoside triphosphates and ribonucleoside triphosphates, into contact with a set of primers, which are present in excess, comprising:
a) a first primer comprising successively from its 5' end towards its 3' end:
   a first polynucleotide segment of arbitrary sequence, and whose presence as constituent of the first primer is optional, the said first segment, when it is present, comprising at least 5 nucleotides,
   a second segment comprising all or part of a sense sequence of a promoter for an RNA polymerase, or comprising at least a portion of the said sense sequence including its 3'-terminal portion,
   and a third segment having the same length as the said upstream sequence and being either homologous to the said upstream sequence, or capable of hybridizing with the said upstream sequence,
b) a second primer comprising successively, from its 5' end towards its 3' end:
   a first optional segment defined like the first segment of the first primer, but not necessarily identical to it,
   a second segment defined like the second segment of the first primer, but not necessarily identical to it,
   and a third segment having the same length as the said downstream sequence and being either homologous to the said downstream sequence, or capable of hybridizing with the said downstream sequence, it being understood that the third segment of one of the first and second primers is homologous to one of the upstream or downstream sequences of the said sequence to be amplified, whereas the third segment of the other primer is capable of hybridizing with the other downstream or upstream sequence,
c) a third and/or a fourth primer comprising either a sequence homologous to the second segment of the first primer and of the second primer respectively, and containing at least a portion of a sense sequence of the said RNA polymerase promoter including its 5'-terminal portion,
   or a sequence homologous to a portion of the first segment of the first and second primer respectively, but not comprising their 5' end, and/or
d) a fifth and/or a sixth primer comprising:
   either a sequence homologous to a portion of the third and of the fourth primers respectively, the said portion not comprising the 3'-terminal nucleotide of the said third or fourth primer,
   or a sequence homologous to at least a portion of the said first segment of the first and of the second primers respectively.

In the present application, the expression "upstream" designates a region situated on the side of the 5' end of the nucleic acid or of the polynucleotide sequence in question, and the expression "downstream" designates a region situated on the side of the 3' end of the said nucleic acid or of the said polynucleotide sequence.

Sequence homologous to another sequence designates a sequence identical to another, or fairly identical to hybridize with a sequence strictly complementary to the sequence with which it is homologous.

The term "heteroduplex" means an RNA/DNA hybrid. The term "homoduplex" designates a DNA/DNA or RNA/RNA hybrid.

The term "nucleoside triphosphates" designates either deoxyribonucleoside triphosphates and/or ribonucleoside triphosphates.

In the method which has just been defined, the starting material comprises a first segment "corresponding" to the sequence to be amplified, which means that it is either the said sequence to be amplified, or the strand complementary to the said sequence to be amplified, it being understood that the method provides in any case an amplification of the two complementary strands, even when the starting material is single-stranded.

The strand displacement capacity which is well known for certain polymerases is associated, inter alia, with the synthesis of DNA for a DNA-dependent DNA polymerase and the synthesis of DNA by an RNA-dependent DNA polymerase. Of course, this strand displacement capacity is more efficient when the relevant polymerases do not have a 5'-3' exonuclease activity. This strand displacement capacity can be provided independently of the polymerases, as defined below.

It should be noted that the polymerases used can have a ribonuclease H activity, insofar as this activity does not prevent the function of the amplification method.

It is easy to see that in the method which has just been described, the third and fourth primers can be identical. Likewise, the fifth and sixth primers can be identical.

Figure 4A:
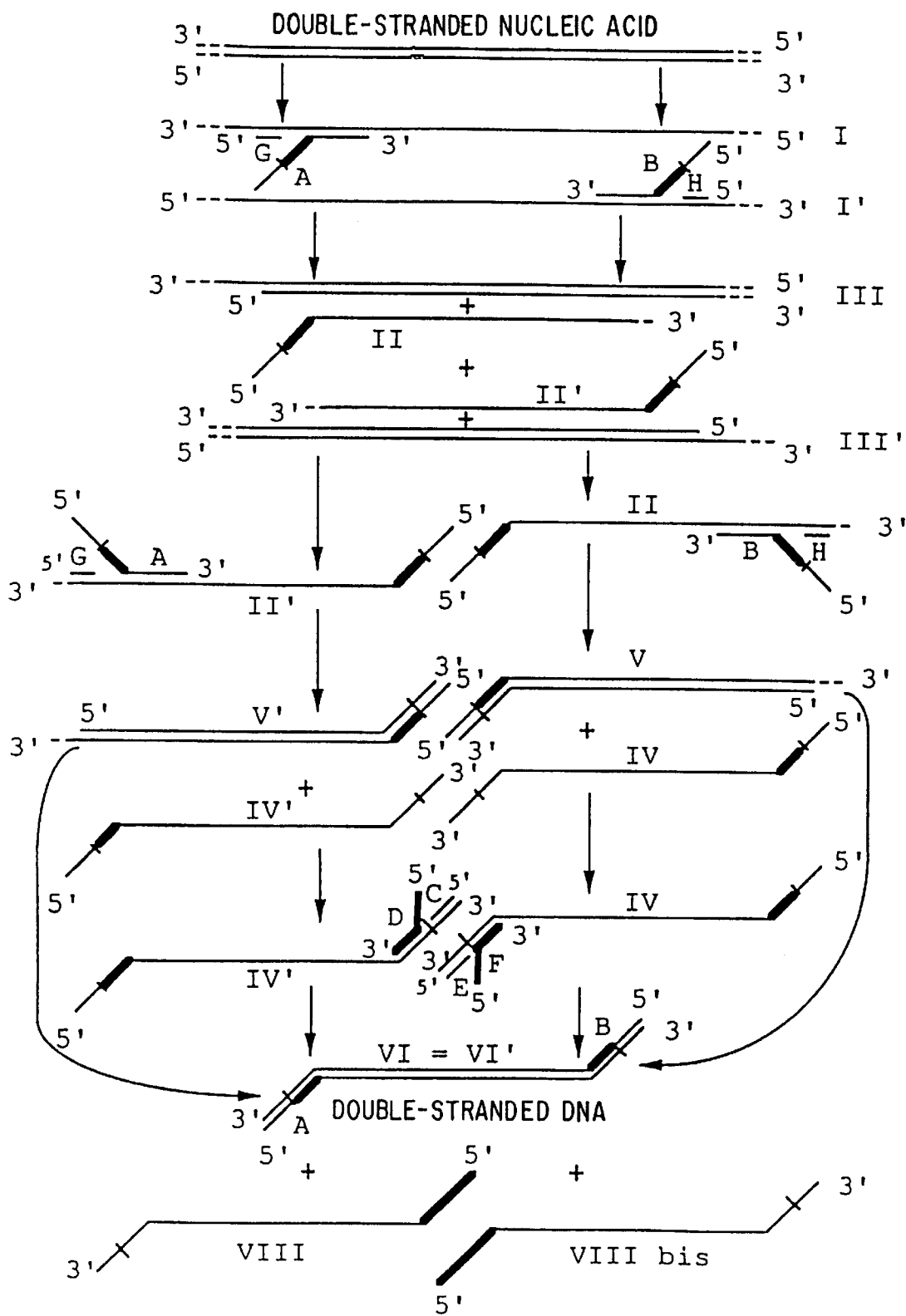
FIG. 4 (comprising FIGS. 4A and 4B) describes another entry route for the amplification method of the invention, by "Transcription Reaction using Displacement", from homoduplex or hetero-duplex, single- or double-stranded DNA or RNA, described in FIG. 6, using primers A and B comprising only a 3' part of the sense sequence of a promoter represented by a short black rectangle, unlike primers D and F which comprise a complete promoter sense sequence represented by a long black rectangle, that is to say that the sequences contained in the primers A and B, in the case of FIGS. 4 and 6, when they are in the form of a double strand, do not form a functional promoter.
Figure 4B:
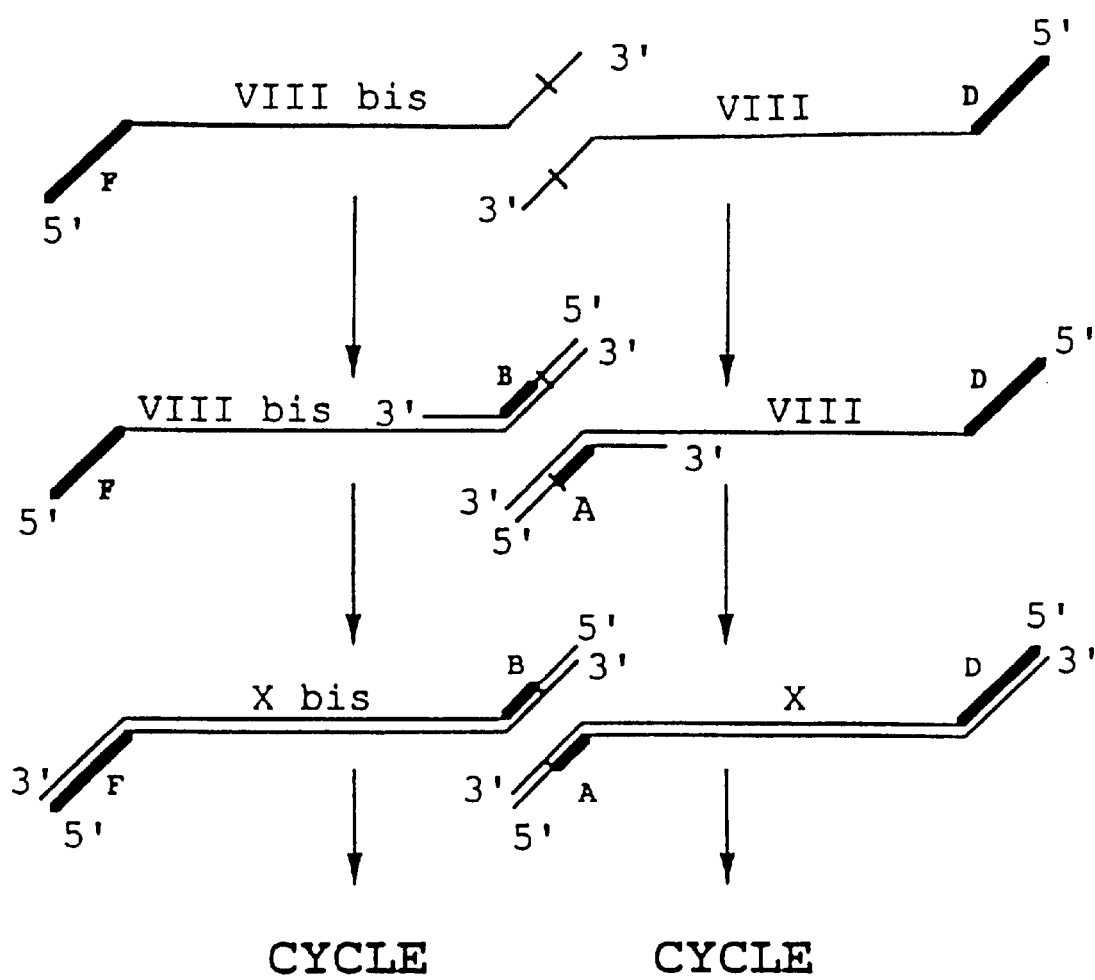

For the amplification method described above to function, it is necessary that the third and fourth primers, if they are present, comprise at least the 5' portion of the sense sequence of the RNA polymerase promoter. This is the case for the primer D represented in FIGS. 4, 5, 6 and 7 and for the primer F represented in FIGS. 4, 5 and 6. These FIGS. 4 and 6 show that it is not necessary that primer A and/or B contain a complete sequence of the promoter for the RNA polymerase. The reaction products derived from A and F on the one hand, and B and D on the other hand should contain a functional sense sequence of the RNA polymerase promoter. "Strand displacement activity" designates the phenomenon by which a biological, chemical or physical agent, for example a DNA polymerase, causes the dissociation of a paired nucleic acid from its complementary strand in a direction from 5' towards 3', in conjunction with, and close to, the template-dependent nucleic acid synthesis. The strand displacement starts at the 5' end of a paired nucleic acid sequence and the enzyme therefore carries out the nucleic acid synthesis immediately in 5' of the displacement site. The neosynthesized nucleic acid and the displaced nucleic acid generally have the same nucleotide sequence which is complementary to the template nucleic acid strand. The strand displacement activity may be situated on the same molecule as that conferring the activity of nucleic acid synthesis, and particularly the DNA synthesis, or it may be a separate and independent activity. DNA polymerases such as *E. coli* DNA polymerase I, Klenow fragment of DNA polymerase I, T7 or T5 bacteriophage DNA polymerase, HIV virus reverse transcriptase are enzymes which possess both the polymerase activity and the strand displacement activity. Agents such as helicases can be used in conjunction with inducing agents which do not possess strand displacement activity in order to produce the strand displacement effect, that is to say the displacement of a nucleic acid coupled to the synthesis of a nucleic acid of the same sequence. Likewise, proteins such as Rec A or Single Strand Binding Protein from *E. coli* or from another organism could be used to produce or to promote the strand displacement, in conjunction with other inducing agents. For further details and a discussion of strand displacement, consult KORNBERG, A. and BAKER T. A. (1992, DNA Replication, 2nd Edition, pp 113–225, Freeman, New York).

Promoter for an RNA polymerase designates a sequence or structure which makes it possible to initiate transcription.

By way of example, there may be mentioned "loop structures" capable of initiating transcription (Møllegaard, N. et al., (1994) PNAS, vol. 91, 3892–3895).

Sense sequence of an RNA polymerase promoter designates the sequence of the double-stranded promoter whose 3' end is contiguous to the site of initiation of transcription which is defined by the same promoter.

Antisense sequence of an RNA polymerase promoter designates the sequence of the double-stranded promoter whose 5' end is contiguous to the nucleotide complementary to the site of initiation of transcription which is defined by the same promoter.

According to a specific embodiment, the polynucleotide used as starting material comprises in addition:

a) upstream of the 5' end of the said second segment comprising all or part of the said sense sequence of the said polynucleotide, a segment homologous to the first segment of one of the first and second primers, and/or b) downstream of the 3' end of the said second segment, comprising the said antisense sequence of the said polynucleotide, a segment capable of hybridizing with the first segment of one of the first and second primers.

It is easy to check that the various starting materials which have just been defined can give rise to an amplification reaction according to the invention.

These starting materials can be prepared, where appropriate, by nucleotide synthesis or by semisynthesis.

In a specific embodiment, the starting polynucleotide may be an RNA or a DNA isolated from a biological sample. In this case, it is possible to obtain an amplification reaction as defined above, starting with the target nucleic acid, in a single stage by adding all the reagents (primers, polymerases and the like) from the beginning of the reaction, optionally after denaturation of the target. This specific embodiment is characterized by the fact that, in order to obtain the said polynucleotide used as starting material in the method described above, the procedure is carried out starting with a target nucleic acid containing the sequence to be amplified and extending, beyond the 3' end of the said sequence to be amplified, via a downstream region, and beyond the 5' end of the said sequence to be amplified, via an upstream region, the said nucleic acid is brought into contact with an excess of nucleoside triphosphates and with:

the said system with DNA polymerase, RNA polymerase and strand displacement activities, and a set of primers containing primers as defined above and containing, in addition, a seventh primer capable of hybridizing with the said region downstream of the target, and an eighth primer capable of hybridizing with a sequence complementary to the said upstream region.

In a specific embodiment of the invention, in order to limit the number of nucleotide primers used in the present invention, it is possible to choose the sequence of the first segment of the first and/or of the second primer as equivalent to the sequence of the seventh and/or the eighth primer.

The invention also relates to a set of primers for implementing a method of amplifying a target nucleic acid, this method being as defined above. This set of primers comprises at least:

a) a primer A1 comprising successively, from its 5' end towards its 3' end:
   a first optional polynucleotide segment of arbitrary sequence, the said first segment, when it is present, comprising at least 5 nucleotides,
   a second segment comprising all or part of the sense sequence of a promoter for an RNA polymerase, or comprising at least a portion of the said sense sequence including its 3'-terminal end,
   and a third segment capable of hybridizing with a target sequence, and/or b) a primer A2 comprising:
   either a sequence homologous to all or part of the second segment of the primer A1, and comprising at least the 5' portion of the sense sequence of the said RNA polymerase promoter,
   or a sequence homologous to a portion of the first segment of the first and second primer, but not comprising their 5' portion, respectively, and/or c) a primer A3 comprising:
   either a sequence homologous to a portion of the primer A2, not comprising the 3'-terminal nucleotide of A2,
   or a sequence homologous to at least a portion of a first segment as defined above which is present in A1.

According to a specific embodiment, the set of primers comprises at least:

a) a primer A1 comprising successively, from its 5' end towards its 3' end:
   a first optional polynucleotide segment of arbitrary sequence, the said first segment, when it is present, comprising at least 5 nucleotides,
   a second segment comprising all or part of the sense sequence of a promoter for an RNA polymerase, or comprising at least a portion of the said sense sequence including its 3'-terminal end,
   and a third segment capable of hybridizing with a target sequence, b) a primer A2 comprising:
   either a sequence homologous to all or part of the second segment of the primer A1, and comprising at least the 5' portion of the sense sequence of the said RNA polymerase promoter,
   or a sequence homologous to a portion of the first segment of the first and second primer, but not comprising their 5' portion, respectively, and/or
   a primer A3 comprising:
   either a sequence homologous to a portion of the primer A2, not comprising the 3'-terminal nucleotide of A2,
   or a sequence homologous to at least a portion of a first segment as defined above which is present in A1.

Figure 3:
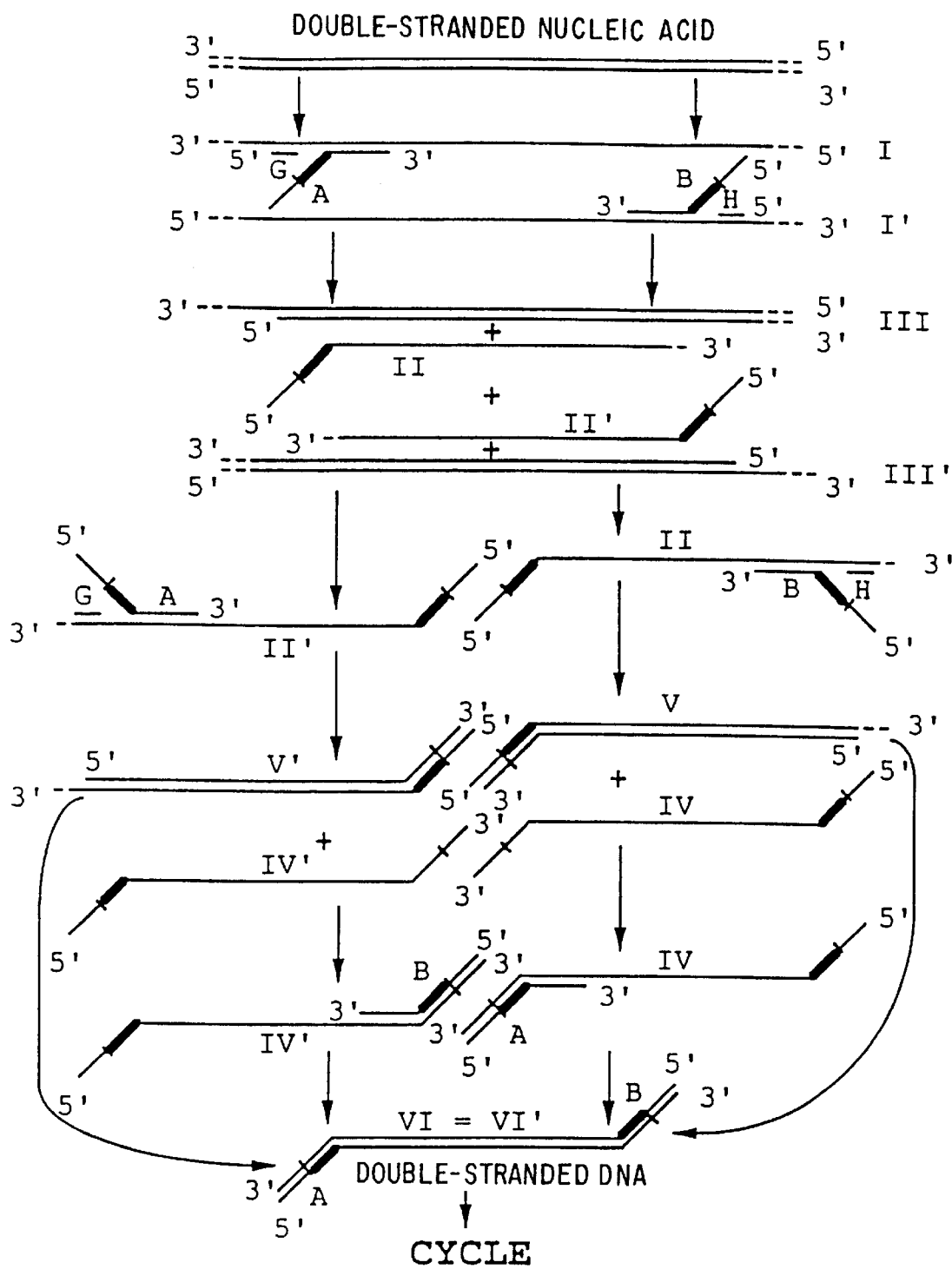
FIG. 3 describes an entry route for the method of amplification of the invention, by "Transcription Reaction using Displacement", from homoduplex or heteroduplex, single- or double-stranded DNA or RNA, which is described in FIG. 5, using primers A and B comprising a complete promoter sense sequence represented by a black rectangle, which, in the form of a double strand, produces a functional promoter.

The scheme for this specific embodiment is given in FIG. 3 in the case of a double-stranded nucleic acid which of course requires prior denaturation.

As evident from FIG. 3, the elongation product of primer A along the target (I) is displaced by the elongation product of primer G, which results in the production of a double-stranded product (III) and of single-stranded DNA (II). Likewise, the elongation product of primer B along the other strand (I') of the target is displaced by the elongation product of H, which results in the production of the double-stranded product (III') and of the single-stranded DNA (II').

The hybridization of primers A and G with the single-stranded DNA (II') similarly results in the production of the double-stranded DNA product (V') and of the single-stranded DNA (IV'). The hybridization of primer B with the single-stranded DNA (IV') results in the double-stranded DNA product (VI) which contains, on each of its strands, the sense sequence (or the portion of the sense sequence present in primer A and in primer B respectively) of an RNA polymerase promoter.

It can be easily seen that by similar hybridizations, elongations and displacements, the single-stranded DNA product (II) results in the same double-stranded DNA product (VI).

In addition, the double-stranded product (V), if it contains a complete sequence of the RNA polymerase promoter, will give a single-stranded RNA transcription product capable of hybridizing with B and H, and the elongation by reverse transcription, with displacement, of these primers results in the production of a single-stranded DNA for which it is easy to check that by hybridization with A followed by elongation, it also makes it possible to obtain the double-stranded DNA product (VI). Analogous reactions, starting with the double-stranded DNA (V'), also result in the double-stranded DNA product (VI). It can be seen in FIG. 3 that the use of the seventh and eighth primers G and H results in the double-stranded DNA product (VI) which is indeed a polynucleotide which can be used as starting material in the general method which was described above.

In a specific embodiment of the invention, in the presence of a single-stranded nucleic acid fragment, a first primer "A" (composed successively, from 5' towards 3', of an arbitrary sequence, followed by a sequence corresponding to all or part of an RNA polymerase promoter or sequence, then by a sequence complementary to the target) hybridizes with its target sequence (I) (FIG. 3). In the presence of a DNA polymerase, nucleotides are added to the 3' end of this primer along the entire length of the target sequence (I). The product of extension is separated from the target nucleic acid strand by strand displacement, following the extension of a primer "G" hybridized upstream of the primer A, which results in the production of the double-stranded product (III) and of the single-stranded DNA (II). A second primer "B" (composed successively, from 5' towards 3', of an arbitrary sequence, followed by a sequence corresponding to all or part of a sequence of an RNA polymerase promoter, then by a target nucleic acid sequence) hybridizes at the 3' end of the product of extension neosynthesized and released into the medium (III). In the presence of DNA polymerase, nucleotides are added to the 3' end of this primer all along the sequence of the neosynthesized strand. This second neosynthesized strand is separated from the first by strand displacement, following the extension of a primer "H" hybridized upstream of primer B with the target. The first primer A can then hybridize with this second released strand and be extended in the presence of a polymerase and of deoxyribonucleoside triphosphates (dNTPs). The double-stranded reaction product of defined size which results therefrom (VI) will then contain, at each end, a functional RNA polymerase promoter sequence preceded in 5' by an arbitrary sequence (FIG. 3).

Figure 5:
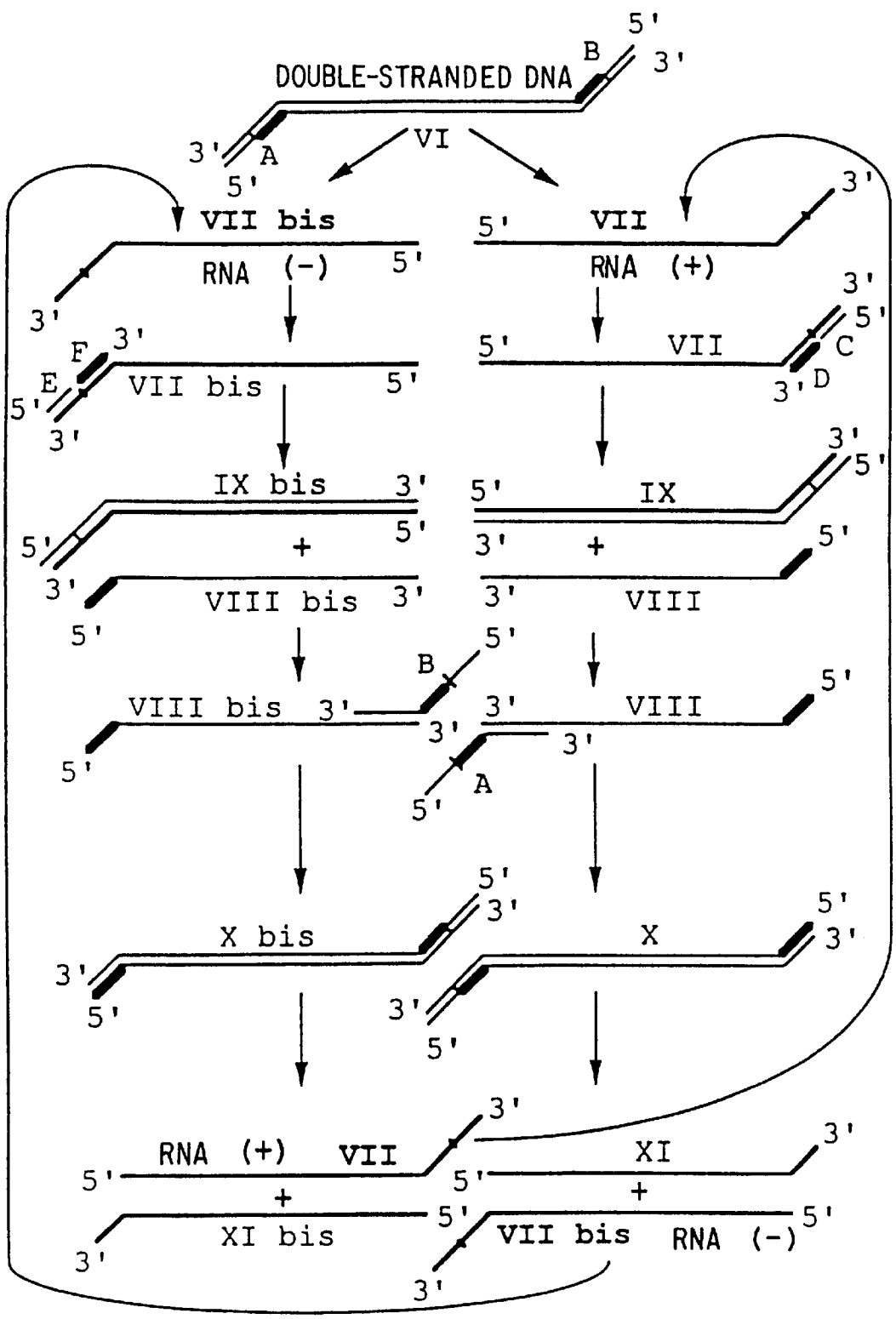
FIG. 5 describes the amplification cycle of the "Transcription Reaction using Displacement" resulting in the exponential accumulation of RNA and DNA corresponding to the two complementary strands of the initial target, using primers A, B, D and F all comprising a complete promoter sense sequence represented by a black rectangle which, in the form of a double strand, produces a functional promoter.
Figure 6:
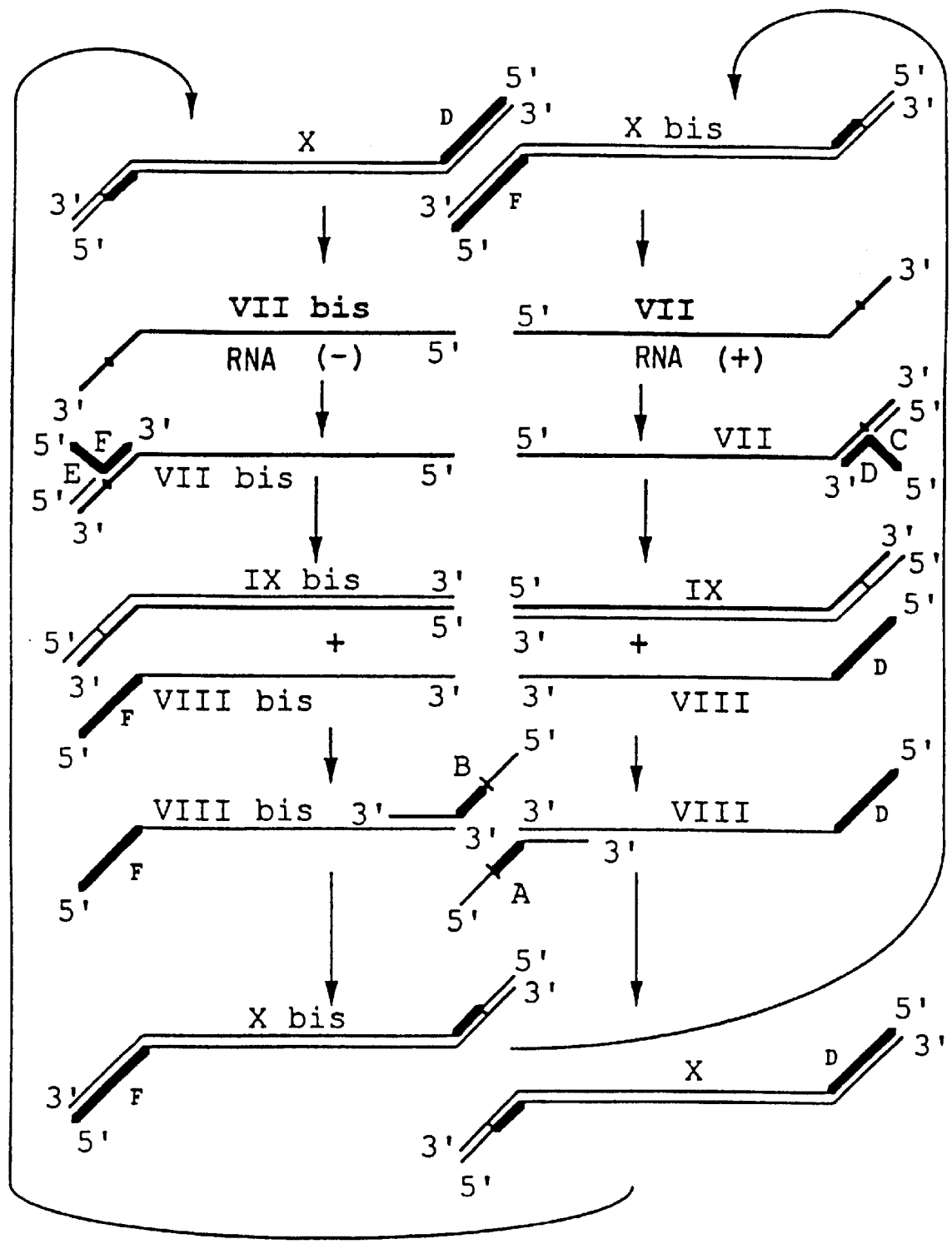
FIG. 6 describes the amplification cycle of the "Transcription Reaction using Displacement" resulting in the exponential accumulation of RNA and DNA corresponding to the two complementary strands of the initial target, using primers A and B comprising only a 3' part of the sense sequence of a promoter represented by a short black rectangle, unlike primers D and F which comprise a complete promoter sense sequence represented by a long black rectangle, that is to say that the sequences contained in primers A and B, in the case of FIGS. 4 and 6, when they are in the form of a double strand, do not form a functional promoter. Consequently, this amplification cycle involves only double-stranded polynucleotides carrying a single functional promoter, allowing the transcription of only one of the two strands.

The product VI obtained is the starting material for the amplification described (FIG. 5).

An RNA polymerase then transcribes using the promoter whose sense sequence is included in A, in the presence of ribonucleoside triphosphates (rNTPs), RNAs (VII) therefore containing at their 3' end the sequence complementary to primer B (FIG. 5). Each transcribed RNA can simultaneously hybridize, at its 3' end, a primer "C" having at its 3' end a sequence containing all or part of the arbitrary sequence of primer B, and downstream of C, a primer "D" having at its 3' end all or part of the sense sequence of the promoter which is included in B. RNA-dependent DNA polymerase extends, in the presence of dNTPs, the 3' end of primer C and simultaneously displaces the strand upstream resulting from the extension of primer D. This results in the release, into the medium, of a single-stranded DNA (VIII) complementary to the RNA transcribed from the promoter of A and comprising at its 5' end the sequence of the promoter of B. The 3' end of this strand can then hybridize with primer A. DNA polymerase extends the 3' end of primer A along the DNA strand and the 3' end of the DNA strand along primer A. The resulting double-stranded reaction product (X), of defined size, then contains, at one end, the functional RNA polymerase promoter sequence included in B, and at the other end, the functional RNA polymerase promoter sequence included in A, preceded in 5' by the arbitrary sequence. RNA polymerase then transcribes from the promoter of B, in the presence of rNTPs, RNAs (VII bis) therefore containing at their 3' end the sequence complementary to primer A.

Likewise, an RNA polymerase then transcribes from the promoter included in B contained in a strand of the double-stranded nucleic acid fragment (VI) of defined size carrying at each end a functional RNA polymerase promoter sequence preceded in 5' by a defined sequence, in the presence of rNTPs, RNAs (VII bis) therefore containing at their 3' end the sequence complementary to primer A (FIG. 5). The 3' end of each transcribed RNA hybridizes simultaneously with a primer "E" having at its 3' end a sequence containing all or part of the sequence "upstream" of primer A, and with a primer "F" having at its 3' end all or part of the sequence of primer A, from the promoter sequence, E and P being chosen such that primer F hybridizes downstream (that is to say towards 3') of E. RNA-dependent DNA polymerase extends, in the presence of dNTPs, the 3' end of primer E and simultaneously displaces the strand downstream resulting from the extension of primer F. This results in the release, into the medium, of a single-stranded DNA (VIII bis) complementary to the RNA transcribed from the promoter of B and comprising at its 5' end the sequence of the promoter of A. This strand can then hybridize, at its 3' end, primer B. DNA polymerase extends the 3' end of primer B along the DNA strand (VIII bis) and the 3' end of the DNA strand (VIII bis) along primer B. The resulting double-stranded reaction product (X bis) of defined size then contains, at one end, the functional RNA polymerase promoter sequence included in A, and at the other end, the functional RNA polymerase promoter sequence included in B, preceded in 5' by the defined arbitrary sequence. RNA polymerase then transcribes from the promoter of A, in the presence of rNTPs, RNAs (VII) therefore containing at their 3' end the sequence complementary to primer B.

The RNAs (VII) containing at their 3' end the sequence complementary to primer B are identical to those transcribed from the template consisting of the double-stranded nucleic acid fragment (VI) of defined size containing, at each end, a functional RNA polymerase promoter sequence, preceded in 5' by a defined arbitrary sequence, from the promoter of A. They therefore bind primers C and D by hybridization and the reaction cycle described above continues.

Likewise, RNAs (VII bis) containing at their 3' end the sequence complementary to primer A are identical to those transcribed from the template consisting of the double-stranded nucleic acid fragment (VI) of defined size containing, at each end, a functional RNA polymerase promoter sequence, preceded in 5' by a defined arbitrary sequence, from the promoter of "B". They therefore bind primers E and F by hybridization and the reaction cycle described above continues.

This results in an exponential amplification of the target between the second segments of primers A and B, resulting in an accumulation of double-stranded DNA and/or RNA corresponding to the amplified target.

The method described in this invention has the advantages of being isothermal, of being able to use only two enzymes, of producing both RNA and DNA, of being capable of being carried out from both target RNA and DNA without any defined end, of not being limited by the nature of the target sequence and of not requiring (ribo)nuclease activity for the separation of the strands of a duplex. In addition, it does not involve the incorporation of modified nucleotides into the amplification products by the polymerases used.

The invention also relates to a kit for carrying out the method as defined above, characterized by the fact that it comprises a set of primers $A_1$, $A_2$, $A_3$ as defined above and at least a second set of primers comprising:

a) a primer B1 comprising successively, from its 5' end towards its 3' end:
   a first optional polynucleotide segment of arbitrary sequence, the said first segment, when it is present, comprising at least 5 nucleotides,
   a second segment comprising all or part of a sense sequence of a promoter for an RNA polymerase, or comprising at least a portion of the said sense sequence including its 3'-terminal end,
   and a third segment capable of hybridizing with a nucleotide sequence complementary to a sequence of the target situated, on the target, upstream of the sequence with which primer A1 is capable of hybridizing, and/or b) a primer B2 comprising:
   either a sequence homologous to all or part of the second segment of the primer B1, and comprising at least the 5' portion of the sense sequence of the said RNA polymerase promoter,
   or a sequence homologous to a portion of the first segment of the first and second primer, but not comprising their 5' portion, respectively, and/or c) a primer B3 comprising:
   either a sequence homologous to a portion of the primer B2, not comprising the 3'-terminal nucleotide of B2,
   or a sequence homologous to at least a portion of a first segment as defined above which is present in B1, the said kit optionally containing, in addition, a seventh and an eighth primer as defined above.

According to a specific embodiment of the kit according to the invention, the second set of primers comprises:

a) a primer B1 comprising successively, from its 5' end towards its 3' end:
   a first optional polynucleotide segment of arbitrary sequence, the said first segment, when it is present, comprising at least 5 nucleotides,
   a second segment comprising all or part of the sense sequence of a promoter for an RNA polymerase, or comprising at least a portion of the said sense sequence including its 3'-terminal end,
   and a third segment capable of hybridizing with a nucleotide sequence complementary to a sequence of the target situated, on the target, upstream of the sequence with which primer A1 is capable of hybridizing, b) a primer B2 comprising:
   either a sequence homologous to all or part of the second segment of the primer B1, and comprising at least the 5' portion of the sense sequence of the said RNA polymerase promoter,
   or a sequence homologous to a portion of the first segment of the first and second primer, but not comprising their 5' portion, respectively, and/or a primer B3 comprising:
   either a sequence homologous to a portion of the primer B2, not comprising the 3'-terminal nucleotide of B2,
   or a sequence homologous to at least a portion of a first segment as defined above which is present in B1, the said kit optionally containing, in addition, a seventh and an eighth primer as defined above.

In the present invention, the sample to be analysed can be isolated from any starting material suspected of containing the target nucleic acid sequence. For animals, and more particularly mammals, the origin of these materials may be blood, the bone marrow, the lymph, the hard tissues (liver, spleen, kidney, lung, ovaries and the like), sputum, smear, faeces, urine. Other origins for the starting materials may be plants, soil samples, food products, as well as any other source suspected of containing biological organisms.

The isolation of the nucleic acids from these starting materials can be carried out in various ways. These processes comprise the use of detergents resulting in lysates, the use of enzymes (lysozyme, proteinase K, for example), ultrasound treatment, mechanical agitation in the presence of beads, or the use of a French press. In some cases, it may be necessary to purify the extracted nucleic acids in order to remove possible contaminants such as nucleases. In this case, the purification of the nucleic acids can be carried out by phenol-chloroform extraction, chromatography, ion exchange, electrophoresis, equilibrium centrifugation or by capture by hybridization on a solid support.

As soon as the nucleic acids are isolated, a brief fragmentation can be carried out by means such as ultrasound treatment, in order to obtain fragments of less than 10 kilobases in size. This then makes it possible to facilitate the initial denaturation, in particular in the case of a double-stranded nucleic acid.

The primers used in the method have a length of between 5 and 100 nucleotides. For example, the length of primers A and B is generally between 30 and 100 nucleotides, and preferably between 40 and 70 nucleotides, whereas the length of primers C, D, E, F, G and H is between 5 and 50 nucleotides, and preferably from 10 to 35 nucleotides. Primers A and B should be substantially homologous or complementary, respectively, in their 3' end, to a sequence of the target (assumed here to be single-stranded), such that under drastic or highly discriminating conditions, their hybridization with their specific site of the target or of its complementary can take place. Primers A and B may contain, at their 5' end, a defined arbitrary sequence, of a length of at least 5 nucleotides. This sequence may optionally be common to A and B but may just as well be different. The said defined sequence may be chosen in any manner, provided that it does not contain any significant homology with the target sequence and that it does not give rise to the formation of dimers between A and B, nor of a secondary structure (for example stem-loop or duplex) within the primer. Downstream of this defined sequence (that is to say towards 3'), primers A and B should contain a sense sequence of a sequence which, with its complementary, has the capacity to bind an RNA polymerase and to initiate the transcription of RNA. These so-called "promoter" sequences, alternatively called sense or antisense of "promoters" are, for example, phage RNA polymerase promoter sequences (for example bacteriophage T7, T3 and SP6). It is known that T7 phage RNA polymerase requires the presence of a specific promoter on the DNA for an efficient transcription of RNA. The sequence of this specific promoter is perfectly characterized (Dunn and Studier, 1983. *J. Mol.*

Biol. 166:477–535) and the high specificity of T7 RNA polymerase transcription from its promoter has been demonstrated (Bailey et al., 1983. Proc. Natl. Acad Sci. 80:2814–2818). These properties can be used in order to produce in vitro RNAs from templates containing a functional double-stranded promoter (Krupp and Söll, 1987. FEBS Lett. 2:271–275). Likewise, RNAs can be transcribed in vitro with the aid of T7 RNA polymerase from synthetic oligonucleotide templates containing a double-stranded promoter (Milligan et al., 1987. Nucl. Acids Res. 15:8783–8798). The article by Krupp (1988 Gene 72:75–89) constitutes a good review of the methods of using phage RNA polymerases and of the strategies useful for the synthesis of RNA in vitro. The promoter sequences used may also be those of promoters for eukaryotic RNA polymerases such as RNA polymerase III (Sharp et al., 1985. Crit. Rev. Biochem. 19:107–144).

Some primers of the present invention comprise homologous sequences. An adjustment of the relative concentrations of the various primers makes it possible to promote differential hybridization for good functioning of the cycles.

In the present method, as soon as the target nucleic acid fragments are obtained, they are denatured, where appropriate, so as to render them single-stranded and to allow the hybridization of primers A and G, and, if the initial nucleic acid is double-stranded, B and H (or vice versa). Increasing the temperature to about 95° C. is preferable for the denaturation, but the separation of the strands can also be carried out by increasing the pH and then neutralizing the medium in order to allow the hybridization of the primers with the target. Before or after the target nucleic acids are denatured, a reaction mixture containing an excess of deoxyribonucleoside triphosphates and ribonucleoside triphosphates, an RNA polymerase and a DNA polymerase is added. In the case where the rise in temperature is used to denature the target nucleic acids, unless thermostable enzymes are used, it is preferable to add the enzymes after denaturation. The reaction mixture necessary for carrying out the amplification reaction according to the invention may also contain polyols such as for example glycerol, sorbitol, polyethylene glycol or denaturing agents and/or solvents such as dimethylformamide, dimethyl sulphoxide (DMSO). These reagents can make it possible to reduce the non-specific hybridization reactions which would generate a possible background noise.

The polymerases used in the method of the invention should preferably lack a strand displacement activity. This activity is a well known property of certain DNA polymerases (Sambrook et al., 1989. Molecular Cloning: A Laboratory Manual, 2nd Edition, pp. 5.33–5.35, Cold Spring Harbor Laboratory, Cold Spring Harbor). The properties of DNA polymerases, and especially of the strand displacement activity of some of them are detailed by Kornberg and Baker (1992, DNA Replication, 2nd Edition, pp. 113–225, Freeman, New York). The strand displacement activity was initially demonstrated for the Klenow fragment of DNA polymerase I of *Escherichia coli* (Masamune and Richardson, 1971. *J. Biol. Chem.*246:2692–2701) which confers on this enzyme the capacity to initiate the replication of a nucleic acid from the 3'OH end of a break in a double-stranded DNA. This strand displacement property is limited in the case where the DNA polymerases possess a 5'-3' exonuclease activity (Lundquist and Olivera, 1982. Cell 31:53–60). This strand displacement activity has also been demonstrated in thermostable DNA polymerases such as Tli DNA polymerase (Kong et al., 1993. *J. Biol. Chem.* 268:1965–1975). In this case, it was also shown that the mutated forms of this enzyme, not having 5'-3' exonuclease activity, have a greater strand displacement capacity. Strand displacement is not a property common to all DNA polymerases since some of them, like T4 DNA polymerases, are not capable of carrying out, on their own, strand displacement. This strand displacement activity has also been demonstrated for T7 DNA polymerase (Lechner et al., 1983. *J. Biol. Chem.* 258:11174–11184) and for HIV reverse transcriptase (Huber et al., 1989. *J. Biol. Chem.* 264:4669–4678). DNA polymerases having a strand displacement capacity, and more particularly capable of initiating polymerization (from 5' towards 3') from the 3'OH end of a break in a double-stranded DNA (FIG. 1) are useful for carrying out the amplification reaction of the present invention. Preferably, a DNA polymerase lacking 5'-3' exonuclease activity is used for carrying out the amplification cycle since the efficiency of the strand displacement activity is greater in enzymes lacking this activity. The Klenow fragment of DNA polymerase I of *Escherichia coli* constitutes an example of polymerase lacking 5'-3' exonuclease activity, likewise polymerases such as T4 DNA polymerase, T7 DNA polymerase or Sequenase (US Biochemical), T5 DNA polymerase or Phi29 DNA polymerase could also be used. However, the present invention also comprises the use of DNA polymerases having this 5'-3' exonuclease activity when the latter does not prevent the implementation of the amplification method. In this case, the yield of the amplification reaction can be enhanced by specific inhibition of the 5'-3' exonuclease activity of DNA polymerases under the reaction conditions used.

The present method of amplification requires a reverse transcription stage, in order to recopy an transcribed RNA into cDNA. This stage can in particular be carried out by the use of a reverse transcriptase of the AMV (Avian Myeloblastosis Virus) or MMLV (Moloney Murine Leukemia Virus) types which are generally commercially available. Any other enzyme possessing an RNA- and/or DNA-dependent DNA polymerase activity may be used in the present invention, provided that it has a strand displacement activity. In the opposite case, the strand displacement activity could be conferred by an indicator agent, a helicase or Rec A type activity. The Rec A properties, especially in the process of single stranded DNA reassociation, of strand capture or of strand assimilation are detailed by Me ENTEE and WEINSTOCK in The Enzymes, vol. XIV, pp. 445–470. The reverse transcription stage can for example be carried out with the aid of *Escherichia coli* DNA polymerase I since it has been demonstrated that this enzyme also has an RNA-dependent DNA polymerase activity (Ricchetti and Buc, 1993. *EMBO* 12:387–396). The present invention can also use, for this purpose, thermostable RNA- and/or DNA-dependent DNA polymerases such as Taq polymerase or Tth polymerase (for a review on the properties of thermostable DNA polymerases, see Rolf et al., 1992. PCR: Clinical Diagnostics and Research, pp. 224–258, Springer-Verlag, Heidelberg).

As a result of the use of the strand displacement properties of DNA polymerases, or of another associated inducing agent, the present invention does not require nuclease activity, whether endonuclease, exonuclease or ribonuclease activity. In particular, the present invention does not require the use of RNase H activity, common to various other amplification techniques mentioned above, an activity conferred by certain reverse transcriptases and which has to be supplemented by the addition of *Escherichia coli* RNase H. In the method of the present invention, it is possible to use MMLV reverse transcriptase, which has a lower RNase H activity than that of AMV (Sambrook et al., 1989. Molecular Cloning: A Laboratory Manual, 2nd Edition, pp. 5.52–5.55, 8.11, 8.17, Cold Spring Harbor Laboratory, Cold Spring Harbor), as RNA- and DNA-dependent DNA polymerase. A form of MMLV reverse transcriptase lacking RNase H activity can also be used in the present invention. The RNase H activity of MMLV reverse transcriptase can indeed be suppressed by deleting a portion of the structural gene for this enzyme (Kotewicz et al., 1988. *Nucl. Acids Res.* 16:265–277), resulting in an enhanced polymerase efficiency compared with the wild-type MMLV reverse transcriptase, and commercially available under the name of "Superscript" (Gerard et al., 1989. *Focus* 11:66–69). The RNase H activity of reverse transcriptase can also be suppressed by performing points mutations in the portion of the gene conferring this polymerase activity (Gerard et al., 1992. *Focus* 14:91–93), resulting in an enzyme also having an enhanced efficiency and a DNA polymerization level greater than Superscript. This enzyme is also commercially available under the name of "Superscript II" (GIBCO-BRL). Another form exists which is commercially available under the name of "StrataScript" (STRATAGENE).

Contrary to various amplification methods, the present invention does not require temperature cycles in order to separate the neosynthesized strand from its template. In this method, a single temperature can be used, as soon as the initial denaturation of the target has taken place, where appropriate. This temperature should be sufficiently high in order to define discriminating hybridization conditions which allow a specific hybridization of the primers with their target. This temperature may be situated for example between 37° C. and 45° C. with conventional enzymatic reagents, but may be higher if thermostable enzymes are used.

FIGS. 3 and 5 describe the method of amplification by Transcription Reaction using Displacement. FIG. 3 describes a possible entry route for the amplification method and FIG. 5 the amplification cycle itself.

After initial denaturation of the target nucleic acid (homo- or heteroduplex single- or double-stranded DNA or RNA), primers A, B, G and H are hybridized with their respective nucleic acid strand (FIG. 3). The simultaneous extension of these primers in the presence of an excess of deoxyribonucleoside triphosphates and of a DNA polymerase (RNA and/or DNA-dependent, depending on whether the target is DNA or RNA) results in the displacement of the DNA strand obtained from the extension of A by extending the strand derived from G and the displacement of the strand obtained from the extension of B by extending the strand derived from H. The single-stranded DNAs obtained by extending primers A on the one hand and B on the other hand can then hybridize primers B and H, and A and G respectively. The extension of G causes the displacement of the strand extending from primer A, and the extension of H causes the displacement of the strand extending from primer B. The two strands of defined length thus released are perfectly complementary and can hybridize with each other, or hybridize with primers B (strand corresponding to the extension of A) or A (strand corresponding to the extension of B), the hybridization of these short primers being more favourable from the thermodynamic point of view. The extension of A and B on their respective strands then results in a double-stranded nucleic acid fragment of defined length corresponding to the target sequence between the second fragments of primers A and B, and flanked at each end by a defined sequence followed downstream by an RNA polymerase promoter.

The entry route presented above (FIG. 3) can also be achieved using a target captured by means of a probe attached onto a solid support. This probe can be immobilized covalently or passively, as described in French Patent No. 91 09057 and International Patent WO 91/19812. This probe immobilization can also be carried out by means of (co) polymers, especially an N-vinylpyrrolidone copolymer, to which probes are coupled by the formation of a conjugate, which conjugate is immobilized onto a solid support by passive adsorption. More particularly, primers A and/or B, or G and/or H can be attached onto a solid support, provided that this attachment is not made via the 3' end of the primers, so that the 3' end of these primers is extendable by a DNA polymerase in the presence of deoxyribonucleoside triphosphates. More particularly, it may be advantageous that all or part of primers A and G on the one hand and B and H on the other hand are linked to each other by means of any linking arm (hydrocarbon or nucleotide for example) and this, from their 5' end. This can make it possible to control and equilibrate the ratio of A relative to G, on the one hand, and of B relative to H, on the other hand, in the amplification reaction described in the present invention.

The double-stranded template thus obtained makes it possible to transcribe the RNAs from each promoter flanking the target sequence (FIG. 5), in the presence of an excess of ribonucleoside triphosphates and the RNA polymerase corresponding to each promoter. To simplify the amplification method of the present invention, this promoter sequence may be a sequence of a promoter of a phage RNA polymerase, the said promoter sequence being the same on primers A and B (for example the consensus of the promoter of the T7 phage RNA polymerase). In the case where primers A and B contain the same promoter sequence, a single RNA polymerase can be used in the amplification reaction.

Figure 7:
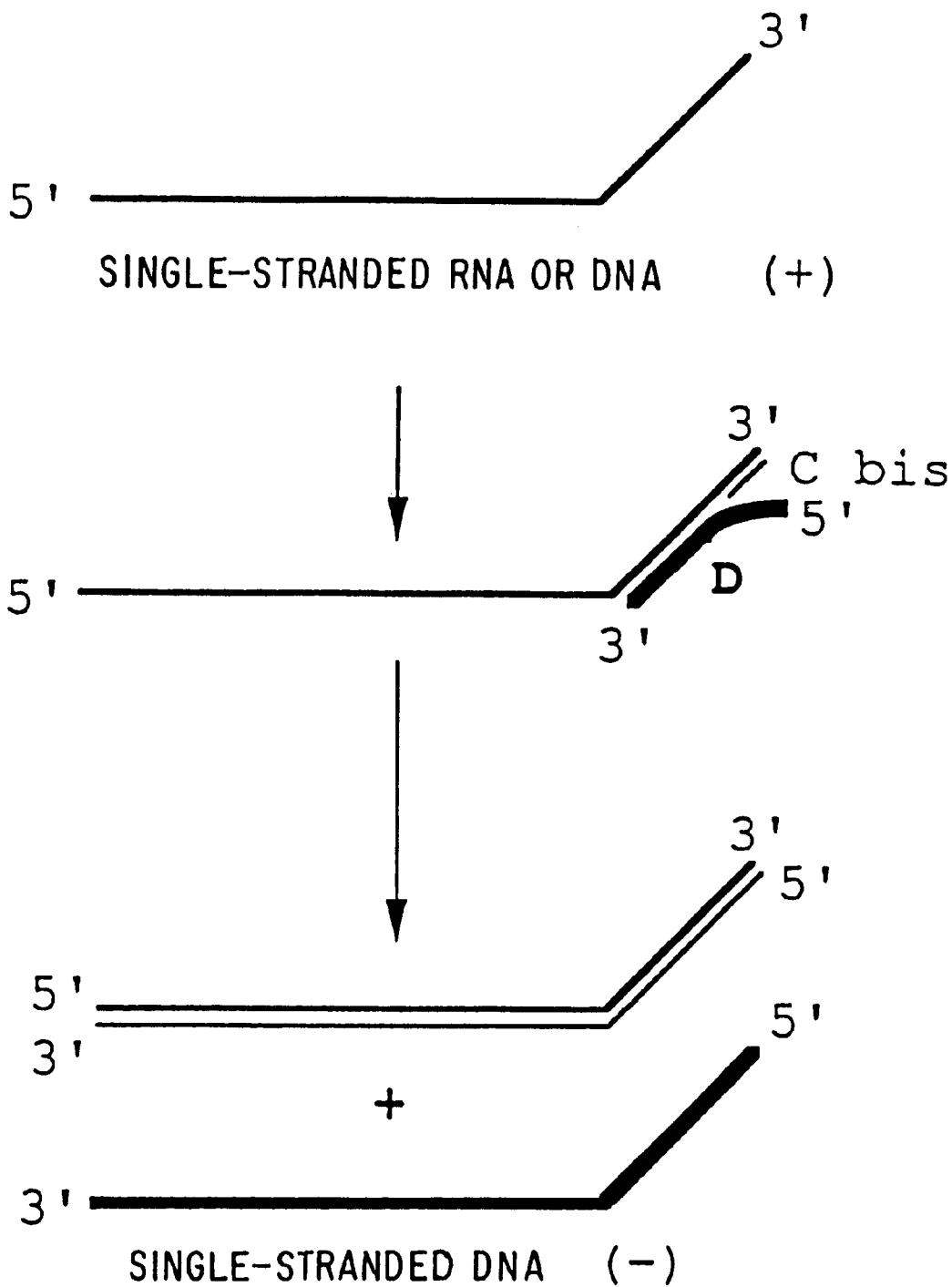
FIG. 7 describes a specific case of primers which can be used to carry out the amplification cycle by transcription using displacement, as described in FIG. 5. Primer D (in bold) corresponds to that described in FIG. 5 and primer C bis is in this case overlapping with primer D. This specific case presumes that the hybridization of the primer C bis with the target is favoured from the thermodynamic point of view compared with the hybridization of the 5' end of primer D.

The RNA transcribed from the promoter contained in A can attach the nucleotide primers C and D. These primers are sufficiently homologous to a portion of B to be able to hybridize, under the reaction conditions, to the RNA transcribed from the promoter of A. These primers C and D may be adjacent, that is to say separated on the target by a gap of at least one nucleotide, or contiguous, that is to say that their 3' and 5' ends are juxtaposed when they are hybridized. Primers C and D may also overlap, that is to say that the 3' end of the primer C has a sequence analogy with the 5' end of primer D. In the case of overlapping primers, the 3' end of the primer C may be sufficiently homologous to the 5' end of primer D, provided that the competitive hybridization between C and D goes in favour of the hybridization of the 3' end of C. FIG. 7 describes a specific case of the invention, where primers C and D overlap. In this case, primer C (called C bis) has the same nucleotide sequence as the 5' end of primer D. In order to promote the competitive hybridization in favour of primer C, especially at its 3' end, it may contain base analogues or modified nucleotides whose hybridization with the RNA results in a duplex of greater stability than that generated by the hybridization of primer D. These modified nucleotides also comprise those modified at the level of the internucleotide linkage (like for example the phosphorothioate, H-phosphonate, alkyl-phosphonate linkages), at the level of the skeleton like for example the alpha-oligonucleotides (French Patent No. 2,607,507) or the PNAs (Egholm et al., 1992. *J. Am. Chem. Soc.* 114:1895–1897). Generally, it is, however, necessary to establish conditions in which the hybridization of C does not prevent the hybridization of the 3' end of D. In the case where C and D overlap, it is advantageous to avoid the 3' end of C being hybridized too close to that of D. A gap of 5 nucleotides constitutes a preferred safety margin to avoid C preventing the hybridization of D. It is preferable that primer D contains the 5' end of the sense sequence of the promoter included, even partially, in primer B, given that the subsequent extension of D should allow the reconstitution of a promoter which can attach an RNA polymerase and direct the initiation of transcription. The lengths of primers C and D may be between 5 and 100 nucleotides and comprise a portion of the target sequence, but not exceeding the length of the target region between primers A and B.

The simultaneous extension of primers C and D on the RNA template, in the presence of a DNA polymerase comprising especially an RNA-dependent activity and of an excess of deoxyribonucleoside triphosphates, results in the displacement of the strand derived from D. The DNA strand thus released can hybridize with primer A. A DNA polymerase (comprising especially a DNA- and/or RNA-dependent activity) can then extend the 3' end of A on the DNA strand and the 3' end of the DNA strand on primer A. The double-stranded DNA thus obtained, of defined size, then has the functional promoter of primer B, as well as the functional promoter of primer A, the said promoter being on this side preceded by an arbitrary sequence.

The double-stranded template thus obtained makes it possible to transcribe RNAs from each promoter situated at the end of this fragment of defined size, in the presence of an excess of ribonucleoside triphosphates and the RNA polymerase corresponding to each promoter. The RNAs transcribed from the promoter of B can then hybridize with primers E and F.

The nucleotide primers E and F are sufficiently homologous to a portion of A to be able to hybridize, under the reaction conditions, to the RNA transcribed from the promoter of B. Like C and D, primers E and F may be adjacent or contiguous, or overlapping. In the case of overlapping primers, the 3' end of primer E may be sufficiently homologous to the 5' end of primer F, provided that the competitive hybridization between E and F is in favour of the hybridization of the end of E. To facilitate the competitive hybridization in favour of the end of primer E, the latter may contain, like C, base analogues or modified nucleotides whose hybridization with the RNA results in a duplex of greater stability than that generated by the hybridization of primer F. It is however necessary to establish conditions in which the hybridization of E does not prevent the hybridization of the 3' end of F. In the case where E and F overlap, it is advantageous to avoid that the 3' end of E is hybridized too close to that of F. A gap of 5 nucleotides constitutes a preferred safety margin. It is essential that the 5' end of primer F contains a minimum sequence of the promoter included in primer A, given that this minimum sequence should allow the subsequent attachment of an RNA polymerase and the initiation of transcription. The length of primers E and F may be between 5 and 100 nucleotides and comprise a portion of the target sequence, but not exceeding the length of the target region between primers A and B.

The simultaneous extension of primers E and F on the RNA template, in the presence of a DNA polymerase comprising especially an RNA-dependent activity and of an excess of deoxyribonucleoside triphosphates, results in the displacement of the strand derived from F. The DNA strand thus released can hybridize with primer B. A DNA polymerase (comprising especially a DNA and/or RNA-dependent activity) can then extend the 3' ends of B on the DNA strand and the extension of the 3' end of the DNA strand on primer B. The double-stranded DNA thus obtained, of defined size, then has the functional promoter of primer A, as well as the functional promoter of primer B, the latter being preceded by an arbitrary sequence.

The double-stranded template thus obtained makes it possible to transcribe RNAs from each promoter situated at the end of this fragment of defined size, in the presence of an excess of ribonucleoside triphosphates and of the RNA polymerase corresponding to each promoter. The RNAs transcribed from the promoter of A can then hybridize with primers C and D. The cycle resulting from the extension of C and D can then start again as described above.

FIGS. 4 and 6 describe a specific case of the method of amplification by "Transcription Reaction using Displacement" in which primers A and B differ from primers A and B of the general method described in FIGS. 3 and 5.

Indeed, primers A and B contain, in addition to the defined arbitrary sequence and the sequence complementary or homologous to the target sequence, only a portion of the sense sequence of a promoter for an RNA polymerase, this portion including the 3' end of this sense sequence of a promoter, and not giving rise, in the form of a double strand, to the generation of a functional promoter, that is to say capable of inducing the initiation of transcription by an RNA polymerase.

Primers C, D, E, F, G and H are as described above in the general method. In particular, primers F and D comprise all or part of a promoter sense sequence.

FIG. 4 describes as follows an entry route for the amplification cycle described by FIG. 6; as in the description of FIG. 3, primers A and G hybridize with the denatured or single-stranded target, and optionally B and H do so if the target is double-stranded. The same enzymes are added to the reaction medium described above. The simultaneous extension of these primers by a DNA polymerase results in the displacement of the DNA strand obtained from the extension of A or B by extending the strand derived from G or H respectively. The single-stranded DNAs obtained can then hybridize with primers B and H, or A and G respectively. The extension of G or H causes the displacement of the product of extension of A or B respectively. The two single strands of DNA of defined length thus generated, carrying an incomplete sense promoter sequence, can hybridize with primers D and C, or F and E respectively. The product of extension of C or E displaces the product of extension of E or F respectively, each generating a single strand of DNA of defined length, and carrying a complete promoter sense sequence, obtained from primers D or F. These DNA strands can hybridize respectively with primers A or B, of which each extension generates a double-stranded nucleic acid corresponding to the target sequence, flanked at one end by a promoter for a whole and functional RNA polymerase, and at the other end by a portion of a non-functional promoter, followed by a defined arbitrary sequence. Like the entry route described in FIG. 3, the entry route described in FIG. 4 may be achieved using a target captured on a solid support.

The double-stranded DNAs thus obtained can enter the amplification cycle described by FIG. 6. Each one allows the transcription of multiple copies of an RNA from a complete functional promoter, one generating a strand comprising the target sequence and the other generating a strand comprising the sequence complementary to the target. These RNA strands can then respectively hybridize either with primers E and F, or with primers C and D. As in the amplification cycle described in FIG. 5, primers C and D, or E and F can be either adjacent, or contiguous, or overlapping (provided that the hybridization on the RNA of the 3' end of F or D is possible). The simultaneous extension of E and F or of C and D on their respective RNA template results in the displacement of the strand derived from F or D respectively. The two DNA strands thus released can hybridize respectively with B or A. Two double strands of DNA of defined length are generated by extending primers A and B on the neosynthesized DNAs and extending the neosynthesized DNAs on these primers. They can again enter into the cycle because they are identical to the two double-stranded DNAs generated during the entry route.

Like the cycle described in FIG. 5, the cycle described in FIG. 6 causes an exponential amplification of RNA and DNA corresponding to the two strands complementary to the initial target.

The nature and the length of the primers used in this invention, the sequences of promoters used and the RNA polymerase concentrations relative to each type of promoter can be chosen so as to favour one amplification route relative to another, so as to obtain preferentially one form or other of DNA or RNA. It is thus possible to predominantly obtain a single-stranded RNA directly detectable in the methods of detecting the amplification products, downstream of the present invention, without a nucleic acid denaturation stage.

The RNA derived from one of the two routes of the amplification method described (FIG. 5) being a substrate for the second, and vice versa, it therefore seems that the method according to the invention is a cyclic amplification technique in which the accumulation of the reaction products occurs exponentially. Each transcription stage using a promoter makes it possible to obtain, using a DNA template, between 500 and 1000 RNA copies. Each RNA makes it possible to obtain a cDNA copy which will result in a DNA template which is available for the transcription of 500 to 1000 RNA copies complementary to the former. The result is therefore that in a single cycle of the said amplification method, there will be a multiplication of the target sequence by a factor of $2.5 \times 10^5$ to $10^6$. For a minimum reaction time for the amplification method (for example one hour or more), it will be possible to produce several reaction cycles, until the amplification reagents such as nucleoside triphosphates and the primers are exhausted, resulting in an amplification whose yield corresponds to $10^9$ to $10^{12}$ DNA and RNA molecules produced for a single initial target molecule. Depending on the concentrations of the reagents used, and especially the various primers, it is possible to favour, by the amplification method, the production of either form of nucleic acids (DNA and/or RNA), and either of the strands of the starting target nucleic acid.

The terms "nucleic acid fragment", "nucleic acid segment" or "oligonucleotide" as used in the present invention, mean a natural DNA or RNA fragment, a natural or synthetic polynucleotide, a synthetic DNA or RNA fragment non-modified or comprising at least one modified base such as inosine, 5-methyldeoxycytidine, 5-dimethylamino-deoxyuridine, deoxyuridine, 2,6-diaminopurine, 5-bromo-deoxyuridine, pseudouridine, pseudoisocytidine or any other modified base allowing the hybridization. This polynucleotide has a length of at least 5 deoxyribonucleotides or ribonucleotides optionally comprising at least one modified nucleotide as described above. This polynucleotide may also be modified at the level of the internucleotide linkage (like for example the phosphorothioate, H-phosphonate, alkyl phosphonate linkages), at the level of the skeleton like for example the alpha-oligonucleotides (French Patent No. 2,607,507) or the PNAs (Egholm et al., 1992. *J. Am. Chem. Soc.* 114:1895–1897). Each of the modifications may be taken in combination.

The term "solid support" as used here includes all the materials on which a nucleic acid fragment can be immobilized for use in diagnostic tests, in affinity chromatography and in separation processes. Natural or synthetic materials, porous or otherwise, magnetic or otherwise, chemically modified or otherwise, can be used as solid support, especially polysaccharides such as cellulose materials, for example paper, cellulose derivatives such as cellulose acetate and nitrocellulose; polymers such as vinyl chloride, polyethylene, polystyrene, polyacrylate or copolymers such as vinyl chloride and propylene polymer, vinyl chloride and vinyl acetate polymer; styrene-based copolymers; natural fibres such as cotton and synthetic fibres such as nylon; ceramics; silica. The supports used in the present invention are a polystyrene polymer, a butadiene/styrene copolymer or a butadiene/styrene copolymer mixed with one or more polymers or copolymers chosen from polystyrene, styrene/acrylonitrile or styrene/methyl methylmethacrylate copolymers, polypropylenes, polycarbonates and the like. Advantageously, the support of the present invention is a polystyrene or a styrene-based copolymer comprising between 10 and 90% by weight of styrene units or silica. The solid supports according to the invention may be, without limitation, in the form of a microtitre plate, a sheet, a cone, a tube, a well, beads and the like.

The term "primer" designates a single-stranded oligonucleotide structure composed of at least five nucleotides. These nucleotides may be deoxyribonucleotides and/or ribonucleotides. These nucleotides can be modified as described above in the paragraph relating to the description of the term "nucleic acid fragment". Once hybridized with a substantially complementary nucleic acid sequence (DNA, RNA, or a chimeric DNA-RNA molecule), the oligonucleotide primers are substrates for the polymerases. The 3'OH end of these primers can be elongated, in the presence of suitable nucleotides and a polymerase, resulting in the synthesis of a strand complementary to the template sequence to which the said primer is hybridized. A primer can also be formed by hybridization of the end of a single-stranded nucleic acid sequence to itself, resulting especially in the formation of hairpin or stem-loop structures. The oligonucleotide primers hybridized with a nucleic acid sequence have the property of attaching polymerases at their 3'OH end.

The following examples illustrate the invention without, however, limiting it. Unless specified, all the methods relating to the carrying out of the experiments described in the examples below were performed in accordance with their description by Sambrook et al. (1989. Molecular Cloning: A Laboratory Manual, 2nd Edition, Cold Spring Harbor Laboratory, Cold Spring Harbor).

EXAMPLE 1

Figure 2:
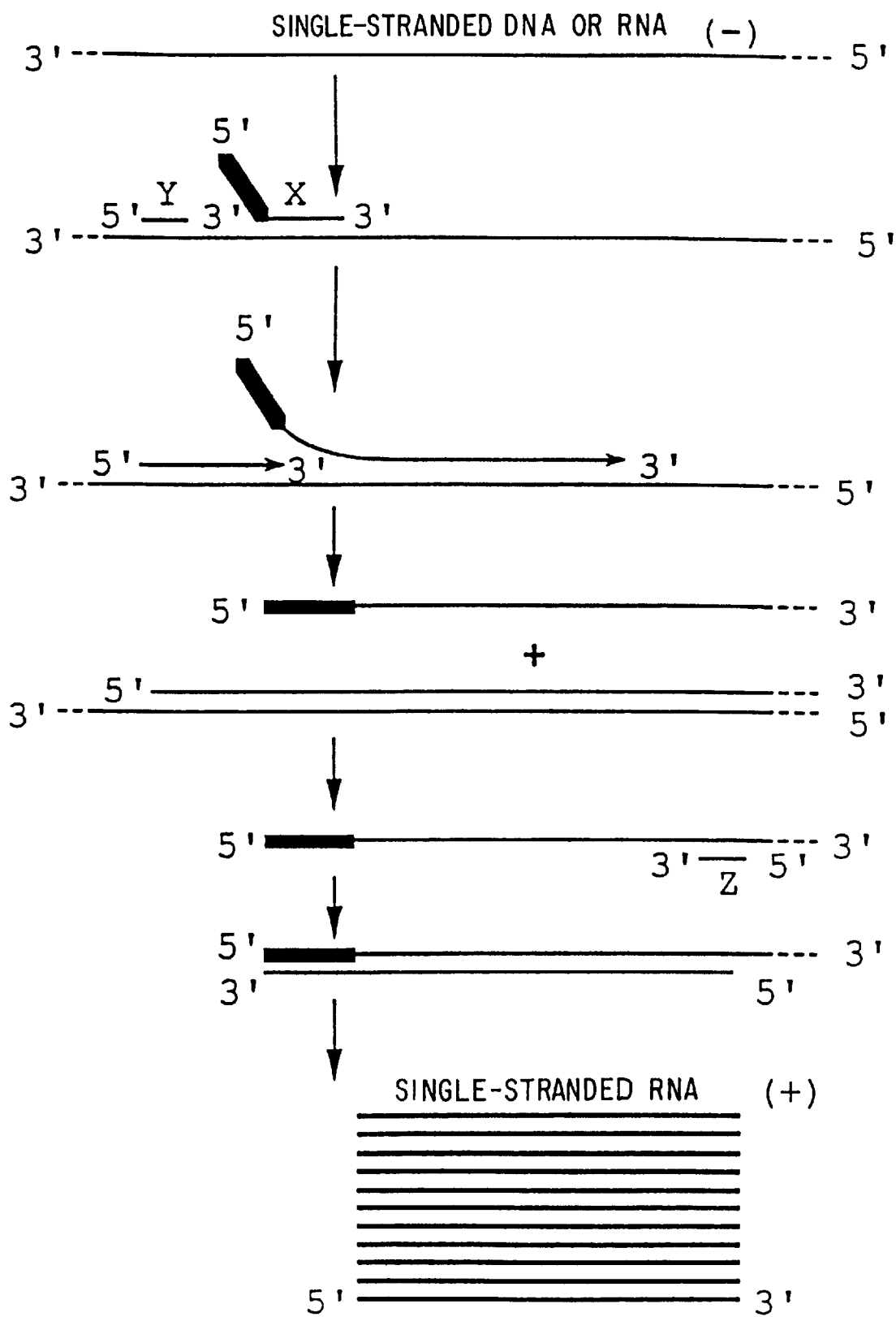
FIG. 2 describes a method of installation of an RNA polymerase promoter by strand displacement for the production of RNAs complementary to a target sequence (RNA or DNA) by transcription, in a homogeneous phase (a single stage and a single temperature). The sequence of the promoter is materialized by black rectangles and the RNAs are represented in bold. The primer X comprises, from 5' towards 3', a sequence comprising the sense sequence of a promoter for an RNA polymerase and a sequence hybridizing with the sequence downstream of the target, the primer Z represents the primer whose extension makes it possible to generate the strand complementary to the fragment obtained from the primer X, and the primer Y represents the "displacement" primer hybridizing downstream of X and whose extension produces the displacement of the product of elongation of X. The signs "+" and "−" refer to sequences belonging to opposite strands of a nucleic acid, that is to say complementary strands.

The feasibility of the amplification technique is demonstrated by separating the various stages involved in it. Since the principle of the method is based on a transcription reaction using displacement, the study of the transcription of a DNA target after displacement has been carried out (FIG. 2). The study model chosen is the sequence of the tem gene encoding β-lactamase, an enzyme which confers resistance to the antibiotic ampicillin. The sequence of this gene is described as SEQ ID No. 1. This sequence is present in the cloning vector pBR322. This nucleic acid can be obtained by extraction of plasmids from a bacterial culture followed by digestion with restriction endonucleases, or it can be prepared by an appropriate amplification technique (Sambrook et al. 1989. Molecular Cloning: A Laboratory Manual, 2nd Edition, Cold Spring Harbor Laboratory, Cold Spring Harbor). The feasibility of installing an RNA polymerase promoter by strand displacement, for the production of RNAs complementary to a target sequence (RNA or DNA) by transcription in homogeneous phase (FIG. 2), has been studied for various DNA polymerases. In this specific case, the RNA polymerase used is that of the T7 phage. The tests are carried out in a final volume of 50 µl and in the 1× reaction buffer described by Milligan et al. (1987. *Nucl. Acids Res.* 15:8783–8798) for the use of T7 RNA polymerase, in the presence of dATP, dCTP, dGTP and dTTP (1 mM each, Pharmacia), of ATP, CTP, GTP and UTP (4 mM each, Boehringer), of 1 U/µl of RNAguard (Pharmacia). The quantity of initial target used is $10^{11}$ copies per test, the concentration of T7 RNA polymerase (New England Biolabs) is 1 U/µl and that of DNA polymerase is 0.1 U/µl. The promoter primer A24 (SEQ ID No: 2) containing a consensus sequence of the T7 phage promoter juxtaposed with a sequence complementary to the target, as well as primer Z, called 1028 (SEQ ID No: 3), are, when present, at a final concentration of 500 nM. The displacement primer Y, called DIS1 (SEQ ID No: 4), is at a variable concentration ranging from 0 to 5 µM. The various reagents, except the enzymatic mixture which is likely to be inactivated by heat (DNA polymerase, RNA polymerase and RNAguard) are brought into contact with the target and denatured for 3 minutes at 95° C. (initial target consisting of double-stranded DNA) or 65° C. (initial target consisting of single-stranded RNA), then cooled on ice for the addition of the enzymatic mixture. The glycerol concentration, due to the addition of the enzymes, is equal to 5%. A 2 hour incubation at 37° C. is then carried out, before stopping the reaction by freezing at −20° C.

A fraction of the reaction mixture (0.2 volume, that is to say 10 µl) is analysed by denaturing polyacrylamide gel electrophoresis, prepared by the method described by Sambrook et al. (1989. Molecular Cloning: A Laboratory Manual, 2nd Edition, Cold Spring Harbor Laboratory, Cold Spring Harbor). The gels are formed by polymerization of a solution containing 15% acrylamide, 7 M urea, 0.26% bisacrylamide, 0.06% ammonium persulphate, 90 mM Tris-borate, 2 mM EDTA, pH 8.3, in the presence of 0.1% TEMED. They are poured into "mini-protean II electrophoresis cell" electrophoresis apparatus (Biorad) and are 1 mm thick. The samples to be analysed are prepared by mixing 10 µl of reaction mixture and 10 µl of a 0.035% xylene cyanole solution, 0.035% bromophenol blue, 1 mM EDTA, 98% formamide. Before loading onto the gel, these samples are denatured at 65° C. for 2 minutes, then rapidly cooled on ice. The electrophoresis is carried out at 150 volts, until the bromophenol blue runs to 1 cm from the bottom of the gel. The gels are then stained for 10 minutes in an ethidium bromide solution at 0.6 µg/ml, and photographed on a UV table (312 nm) using an MP4 apparatus (Polaroid).

The products separated by electrophoresis are transferred onto Hybond N. nylon membrane (Amersham) using a "mini trans-blot electrophoretic transfer cell" apparatus (Biorad) in a 45 mM Tris-borate buffer containing 1 mM EDTA, pH 8.3, at 4° C., under an electric field of 35 volts. hour$^{-1}$. cm$^{-1}$. The membranes are then dried for 5 minutes at 80° C. and then nucleic acids are fixed onto the membrane by exposure to UV radiation (312 nm) for 3 minutes.

The membranes are prehybridized by incubating at 37° C. for 60 minutes in 4 ml of 0.1 M sodium phosphate buffer pH 7.0 containing 0.5 M sodium chloride, 1 mM EDTA, 0.65% SDS, 0.14 mg/ml salmon DNA and 2% polyethylene glycol 6000 (PEG). The hybridization is carried out by incubating for 60 minutes at 37° C. in 5 ml of the same buffer containing, at a concentration of 200 ng/ml, the oligonucleotide A28 (SEQ ID No: 5), complementary to the expected product of transcription (corresponding to the strand of, SEQ ID No: 1) of the tem gene, and labelled with horseradish peroxidase by coupling with 5' according to the method described earlier in International Patent WO 91/19812. After 3 washes of 30 seconds in 50 ml of 1× PBS buffer (Sambrook et al., 1989. Molecular Cloning: A Laboratory Manual, 2nd Edition, Cold Spring Harbor Laboratory, Cold Spring Harbor) containing 0.05% Tween 20, the hybridized oligonucleotide is revealed by the peroxidase activity in the presence of 10 mg of diaminobenzidine tetrahydrochloride dihydrate (DAB) in 20 ml of 20 mM sodium phosphate buffer pH 7.2, containing 150 mM sodium chloride, 2 mg/ml bovine serum albumin. After incubation at room temperature and protected from light for 15 minutes, the reaction is stopped by rinsing with distilled water.

Tests of transcription dependent on displacement were carried out using a target consisting of the plasmid pBR322 previously cleaved with the endonuclease AluI and then purified ($10^{11}$ copies/test). The DNA polymerase used is a DNA-dependent DNA polymerase, the Klenow fragment (Boehringer, 5 U/test), in the absence or in the presence of various concentrations of displacement primer Y, called DIS1 (SEQ ID No: 4), namely: 5 µM (about $10^{14}$ copies), 500 nM, 50 nM, 5 nM or 0. 5 nM. A control for T7 RNA polymerase activity was previously made by preparing a double-stranded DNA fragment by PCR, from the AluI-cleaved pBR322 target, and with the aid of primers A24 (SEQ ID No: 2) and 1028 (SEQ ID No: 3). of course, the double-stranded fragments with defined ends comprising at least one promoter, can be prepared for example by cloning a sequence into a plasmid containing a promoter, digesting with restriction enzymes and purifying on agarose gel followed by electroelution. The 285 base pair product thus obtained contains, in this case, the T7 phage promoter at one end and its transcription by T7 RNA polymerase makes it possible to obtain an RNA of 263 bases corresponding to the reaction product expected during the tests of transcription dependent on displacement. The marker for T7 RNA polymerase activity is made by incubating $10^{11}$ copies of the 285 base pair fragment under the conditions described above, but in the absence of DNA polymerase and dNTPs. This reaction is carried out for two hours, in parallel with the displacement tests.

Figure 8:
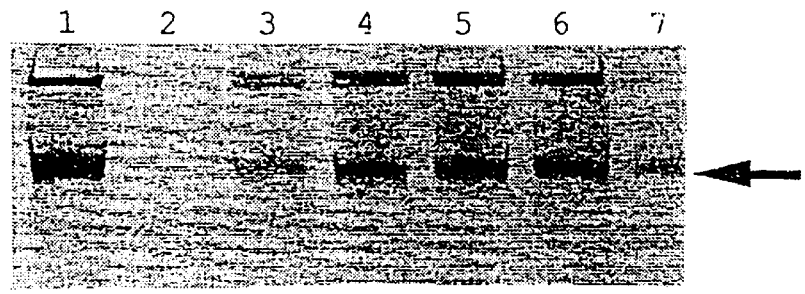
FIG. 8 represents the analysis of the products of transcription using displacement, by electrophoretic separation on a polyacrylamide gel, transfer onto a membrane and hybridization, as described in Example 1. The arrow indicates the expected product of transcription, of 263 bases. Lane 1 corresponds to the transcription control. Lane 2 corresponds to the test in the absence of displacement primer. Lanes 3 to 7 correspond to tests containing 5 mM, 500 nM, 50 nM, 5 nM or 0.5 nM respectively.

FIG. 8 illustrates the results obtained during the tests of strand displacement by the Klenow fragment, in the presence of variable quantities of displacement primer Y. As expected, the results show that the presence of a transcription product is limited to the samples containing a displacement primer Y. The positive transcription results in the presence of displacement primer Y demonstrate the strand displacement capacity of the Klenow fragment. Indeed, the presence of RNAs complementary to the tem target and of size corresponding to the gap between primers X and Z on the ten target, that is to say which are identical to those derived from the transcription control, results from the transcription using a double-stranded DNA fragment identical to that of the T7 RNA polymerase transcription control and containing, like the latter, a functional RNA polymerase promoter (double strand). This fragment can only be obtained, under the reaction conditions described, by extending primer Z hybridized with the product of extension of the promoter primer X (FIG. 2) containing the T7 promoter. Now, the hybridization and extension of primer Z is only possible in the presence of a product of extension of the promoter primer X in the form of a single strand. The presence of this extension product in the form of a single strand can only result from the extension of the displacement primer Y which causes the release of the product of extension of the promoter primer X.

The results also show that the intensity of the final transcription product varies as a function of the concentration of the displacement primer Y in the tests. The quantity of transcribed material being proportional to the quantity of template available for the T7 RNA polymerase, it therefore appears that the quantity of template synthesized by displacement and extension differs as a function of the quantity of displacement primer Y used in a test. The concentration of primer Z being constant and in excess, the quantity of double-stranded template available depends on that of the single-stranded product of extension of the promoter primer. It is therefore the case that the quantity of extension product released (single strand) varies as a function of the concentration of displacement primer in the tests. Under the conditions used, a displacement primer concentration of 50 nM (that is to say 10 times the quantity of target present), corresponding to a displacement primer/promoter primer ratio equal to $1/10$, gives the best yield of displacement and therefore of transcription. These results show the influence of the displacement primer/promoter primer ratio for the yield of displacement of a nucleic acid strand by extension of a primer situated upstream of the latter. On either side of this optimum, the displacement yield decreases substantially: if the concentration of displacement primer increases, the thermodynamic conditions favour the hybridization of the latter with the target and therefore its extension, at the expense of the hybridization, and then extension of the promoter primer; likewise, the results show that if the displacement primer concentration decreases, the probability of hybridization of the latter upstream of the promoter primer decreases and consequently the probability of extension for the displacement of the strand situated downstream decreases.

This example demonstrates the possibility of using the strand displacement properties of a polymerase for installing a promoter sequence on a given target sequence. This method has the advantage of allowing the production of a DNA template for the RNA polymerase, without the need for a thermal or chemical denaturation stage or without requiring the action of a nuclease type enzymatic activity to release the product of extension of a promoter primer on a single-stranded nucleic acid. Using a combined transcription stage, it is therefore possible to synthesize a large copy number of RNA corresponding to the target sequence between the two primers X and Z. FIG. 8 shows that the target sequence cannot be detected by the method used without a stage for amplification for transcription (lane 2). In contrast, the use of a DNA polymerase having strand displacement activity, associated with a displacement primer, makes it possible to obtain a template allowing the synthesis of multiple strands of RNA corresponding to the target, and whose number allows their detection, indicating the presence of the target in the initial sample. This example therefore demonstrates the usefulness of the method for installing an RNA polymerase promoter by strand displacement for the production of multiple RNA strands complementary to a target sequence by transcription in a homogeneous phase (a single stage and a single temperature). This method makes it possible to directly obtain transcripts of a target sequence by addition of a reaction mixture comprising a primer Y, a primer X, a primer Z, deoxyribonucleoside triphosphates and ribonucleoside triphosphates, a DNA polymerase having a strand displacement capacity and an RNA polymerase, to a previously denatured nucleic acid target, especially in the case of a double-stranded target. The method is therefore composed of a single stage, without subsequent or intermediate addition of reagents, or the use of enzymatic activity, in particular nuclease activity.

EXAMPLE 2

Figure 9:
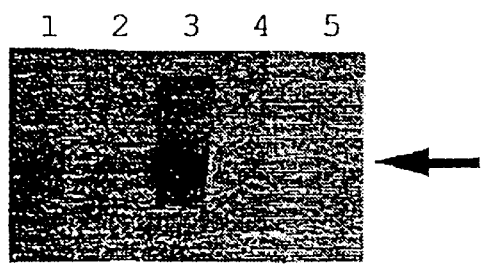
FIG. 9 represents the analysis of the products of transcription using displacement, by electrophoretic separation on a polyacrylamide gel, transfer onto a membrane and hybridization, as described in Example 2. The arrow indicates the expected product of transcription, of 263 bases. Lane 1 corresponds to the size marker of 285 base pairs obtained by PCR with the aid of primers A24 (SEQ ID No: 2) and 1028 (SEQ ID No: 3). The tests were carried out in the absence of reverse transcriptase and T7 RNA polymerase (lane 2) or in the presence of enzymes, with three types of primers X, Y and Z (lane 3), without displacement primer Y (lane 4) or without primer Z (lane 5).

The feasibility of the present invention also implies that the transcription in the homogeneous phase, as described in Example 1, can also be carried out using an RNA molecule. This RNA molecule may be either the initial target, the determination of whose presence by amplification is made possible by the present invention, or an intermediate product of the cycle of the amplification method (FIG. 5). This intermediate product may be, by way of example, the RNA obtained by transcription in the case of Example 1. This feasibility presupposes the use of a DNA polymerase, both RNA- and DNA-dependent, which has a strand displacement capacity. In order to demonstrate this feasibility, RNAs, that is to say corresponding to the sequence complementary to the tem sequence (SEQ ID No: 1), were synthesized in vitro with the aid of T7 RNA polymerase, under the reaction conditions of the MEGAscript kit (Ambion), using $10^{12}$ copies of DNA template. In order to do this, a double-stranded DNA template was synthesized by PCR, from pBR322, and with the aid of PROANTI (SEQ ID No: 6) and ORF1 (SEQ ID No: 7) primers. The 889 base pair product thus obtained contains, in this case, at one end, the T7 phage promoter and its transcription by T7 RNA polymerase makes it possible to obtain an RNA of 867 bases corresponding to the sequence complementary to the sequence of the tem gene (SEQ ID No: 1). The synthesized RNAs are treated with DNase I in order to remove the template DNA, purified by phenol/chloroform extraction and precipitated with ethanol in the presence of ammonium acetate salts. The RNAs thus obtained are taken up in water previously treated with diethyl pyrocarbonate (DEPC), analysed by denaturing polyacrylamide gel electrophoresis and assayed by absorbance at 260 nm. A quantity equivalent to $10^{11}$ copies of target RNA (5 nM final) is used per test and the reaction conditions are identical to those described in Example 1, in the presence of the primers X, Y and Z described above. However, the DNA polymerase used within the framework of these tests is the AMV virus reverse transcriptase (Seikagaku) and the displacement primer/promoter primer ratio set at the optimum determined above ($1/10$) was used, which corresponds to a final displacement primer concentration equal to 50 nM final. The analysis of the reaction products is carried out as described in Example 1, by electrophoretic separation, transfer onto a membrane and hybridization with the aid of probe A28 (SEQ ID No: 5) labelled with horseradish peroxidase. FIG. 9 illustrates the results obtained during the different reaction tests. A quantity equivalent to $10^{12}$ copies of PCR fragment of 285 base pairs, containing a T7 promoter at one end, obtained with the aid of primers A24 (SEQ ID No: 2) and 1028 (SEQ ID No: 3), was loaded (lane 1) to serve as size marker for the expected RNA (263 bases), corresponding to the transcription of an identical fragment, during the tests carried out. The tests were carried out in the absence of reverse transcriptase and T7 RNA polymerase (lane 2), and in the presence of enzymes, with primers X, Y and Z (lane 3), without displacement primer Y (lane 4) or without primer Z (lane 5). The expected RNA of 263 bases is detected only from the test containing all the enzymatic reagents and the primers, whereas in the absence of displacement primer, no transcription product is obtained. This result therefore confirms the feasibility of the strand displacement by the action of a DNA polymerase and demonstrates the feasibility of the displacement on an RNA template, by virtue of the strand displacement capacity of AMV reverse transcriptase. The latter is therefore capable, during the extension of a primer situated upstream of a previously extended primer, of separating an RNA-DNA heteroduplex. The stability of the latter being known to be greater than that of a DNA—DNA homoduplex, it is a fortiori likely that this reverse transcriptase is capable, by primer extension, of displacing a DNA strand hybridized with a DNA target. Although an RNase H activity associated with AMV reverse transcriptase is described, no transcription product is obtained in the absence of displacement primer. This suggests that the buffer conditions used in these tests are not appropriate for this RNase H activity or that the sequence of the RNA target used is not very sensitive to the action of the latter. The RNA of the target RNA-cDNA duplex cannot therefore be degraded and the product of extension of the promoter primer cannot therefore be released for the hybridization and the extension of primer Z on the latter. This result therefore demonstrates, in addition to the strand displacement capacity of AMV reverse transcriptase, the total lack of efficiency, under these conditions, of the separation of a cDNA from a cDNA-RNA heteroduplex by the action of the RNase H associated with the AMV reverse transcriptase, justifying the use of exogenous *Escherichia coli* RNase H in the transcriptional amplification methods described above, such as NASBA, 3SR or LAT. In the absence of primer Z (but in the presence of displacement primer Y), no transcription product is obtained, which shows that no self-priming reaction occurs at the 3' end of the cDNA derived from the extension of the promoter primer, under the conditions of the present reaction, although this property has been described in reverse transcriptases under specific conditions.

This example therefore demonstrates the efficiency of the method for installing an RNA polymerase promoter by strand displacement for the production of RNAs complementary to an RNA target sequence, by transcription in a homogenous phase (a single stage and a single temperature) as described in FIG. 2, and to produce multiple RNA strands complementary to a given target RNA strand. The method is therefore composed of a single stage, without subsequent or intermediate addition of reagents, and requires no nuclease, in particular RNase H, activity for the separation of a cDNA from an RNA-DNA heteroduplex. In particular, under the reaction conditions, AMV reverse transcriptase shows no RNase H activity which would allow the release, in the absence of displacement primer, of the strand extended from the promoter primer on an RNA template. The strand displacement capacity of AMV reverse transcriptase therefore demonstrates the feasibility of the amplification cycle and consequently the exponential nature of the accumulation of the reaction products from an RNA or a DNA target (FIG. 5).

EXAMPLE 3

Figure 10:
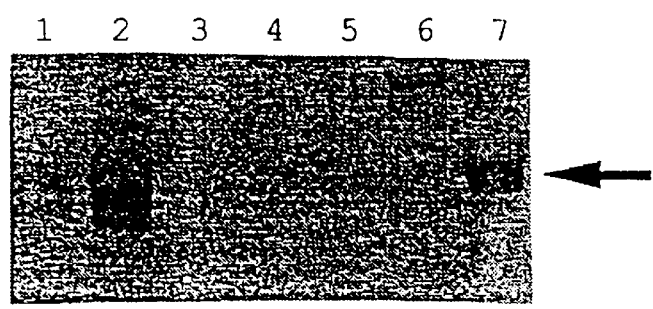
FIG. 10 represents the analysis of the products of transcription using displacement, by electrophoretic separation on a polyacrylamide gel, transfer onto a membrane and hybridization, as described in Example 3. Lane 1 corresponds to the size marker of 285 base pairs obtained by PCR with the aid of primers A24 (SEQ ID No: 2) and 1028 (SEQ ID No: 3). Lane 2 corresponds to the target transcription control of 285 base pairs in the presence of T7 RNA polymerase. Lanes 3 to 6 correspond to the tests carried out in the absence of one of the reagents, namely T7 RNA polymerase (lane 3), reverse transcriptase (lane 4), primer Z (lane 5) or the displacement primer Y (lane 6). Lane 7 corresponds to the test in the presence of all the reagents, as described in Example 3.

In order to confirm the feasibility of the separation of a DNA molecule from a DNA-RNA heteroduplex by strand displacement, and this independently of any residual RNase H activity intrinsic to certain reverse transcriptases, tests were carried out using an MMLV reverse transcriptase lacking RNase H activity. Such an enzyme, obtained by genetic engineering, is commercially available under the name "Superscript$^{II}$" (GIBCO-BRL). The tests were carried out as in Example 2, using the same RNA target, with the aid of the primers X, Y and Z described above. Superscript$^{II}$ is added to a final concentration of 4 U/$\mu$l (200 U/test) and the displacement and promoter primers are present at a ratio of $\frac{1}{10}$. The reaction products are analysed in the manner described in Example 1. The results obtained are presented in FIG. 10. It appears that the presence of a transcription product is limited to the sample containing a displacement primer Y (lane 7), which confirms the strand displacement capacity of MMLV reverse transcriptase lacking RNase H activity. In the absence of displacement primer (lane 6), no transcription signal is obtained, confirming the validity of the separation of a DNA from an RNA-DNA heteroduplex by the strand displacement properties of reverse transcriptases. In the absence of primer Z (lane 5), no transcription product is obtained, which confirms, as in Example 2, that the MMLV reverse transcriptase "Superscript$^{II}$" does not carry out the self-repriming of the 3' end of the cDNA under these reaction conditions.

This example therefore confirms the feasibility of the method of amplification by transcription using displacement, from an RNA target, and this in a manner completely independent of the RNase H activities which may be present in the reaction medium. The amplification method described in the present invention can therefore be carried out with the aid of a reverse transcriptase and an RNA polymerase, without any other additional enzymatic activity.

EXAMPLE 4

Figure 11:
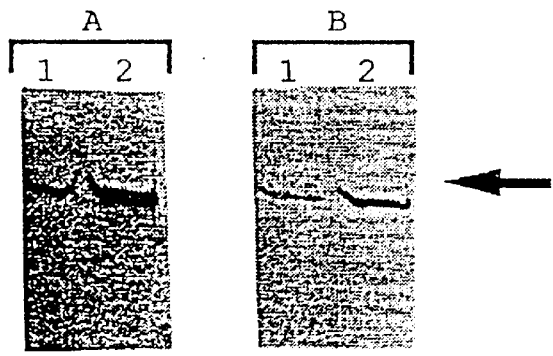
FIG. 11 represents the analysis of the products of transcription from a nucleic acid flanked by two promoters oriented for the transcription of either one of the nucleic acid strands, by electrophoretic separation on a polyacrylamide gel, transfer onto a membrane, and hybridization either with a probe A28 (SEQ ID No 5) (panel A), or with a probe A19 (SEQ ID No 11) (panel B), which respectively detect either +RNAs or −RNAs, as described in Example 4. Lane 1 corresponds to the size marker of 275 base pairs. Lane 2 corresponds to the transcriptional tests.
Figure 12:
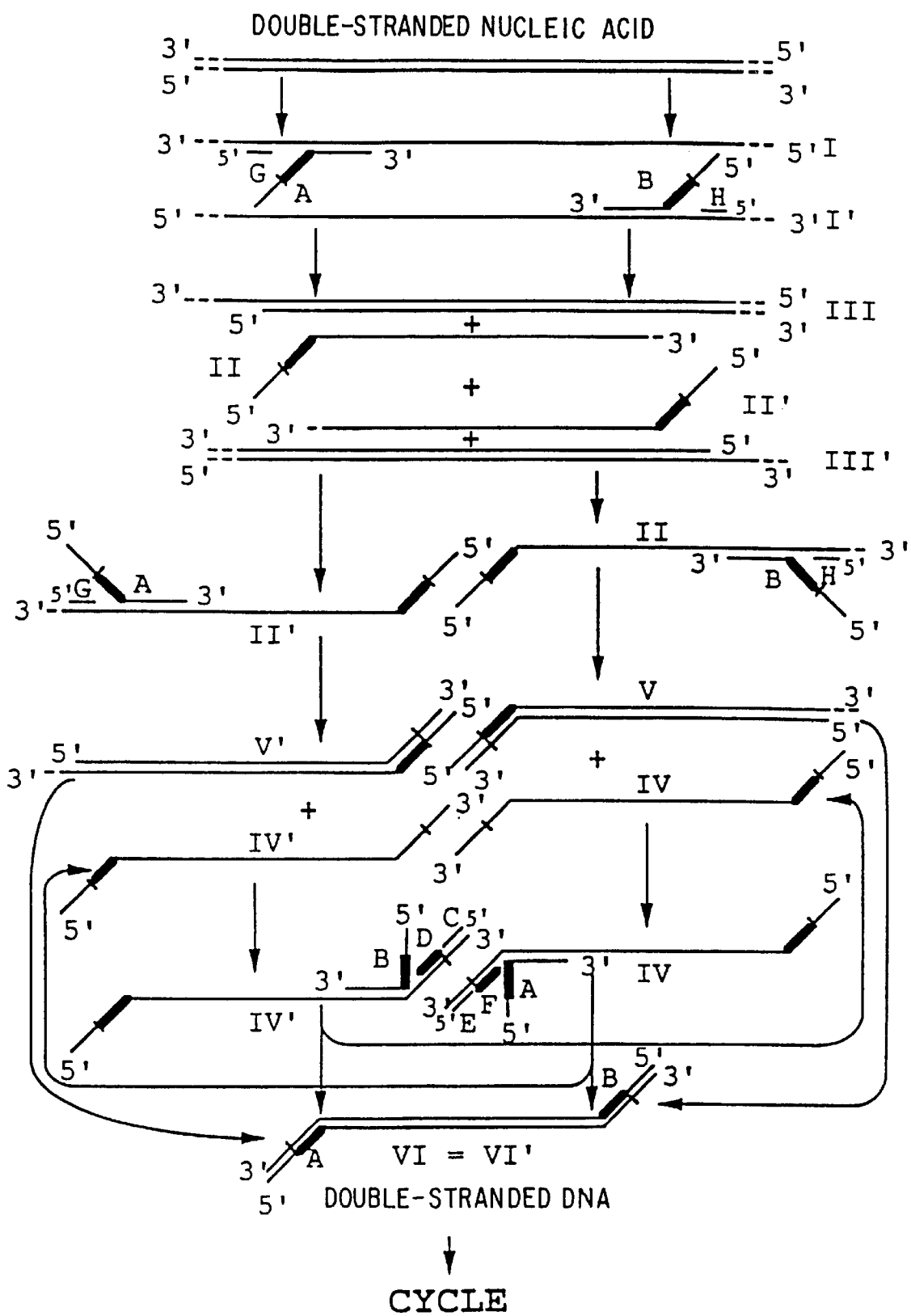
FIGS. 12 and 13 represent another embodiment of FIGS. 3 and 5 respectively.
Figure 13:
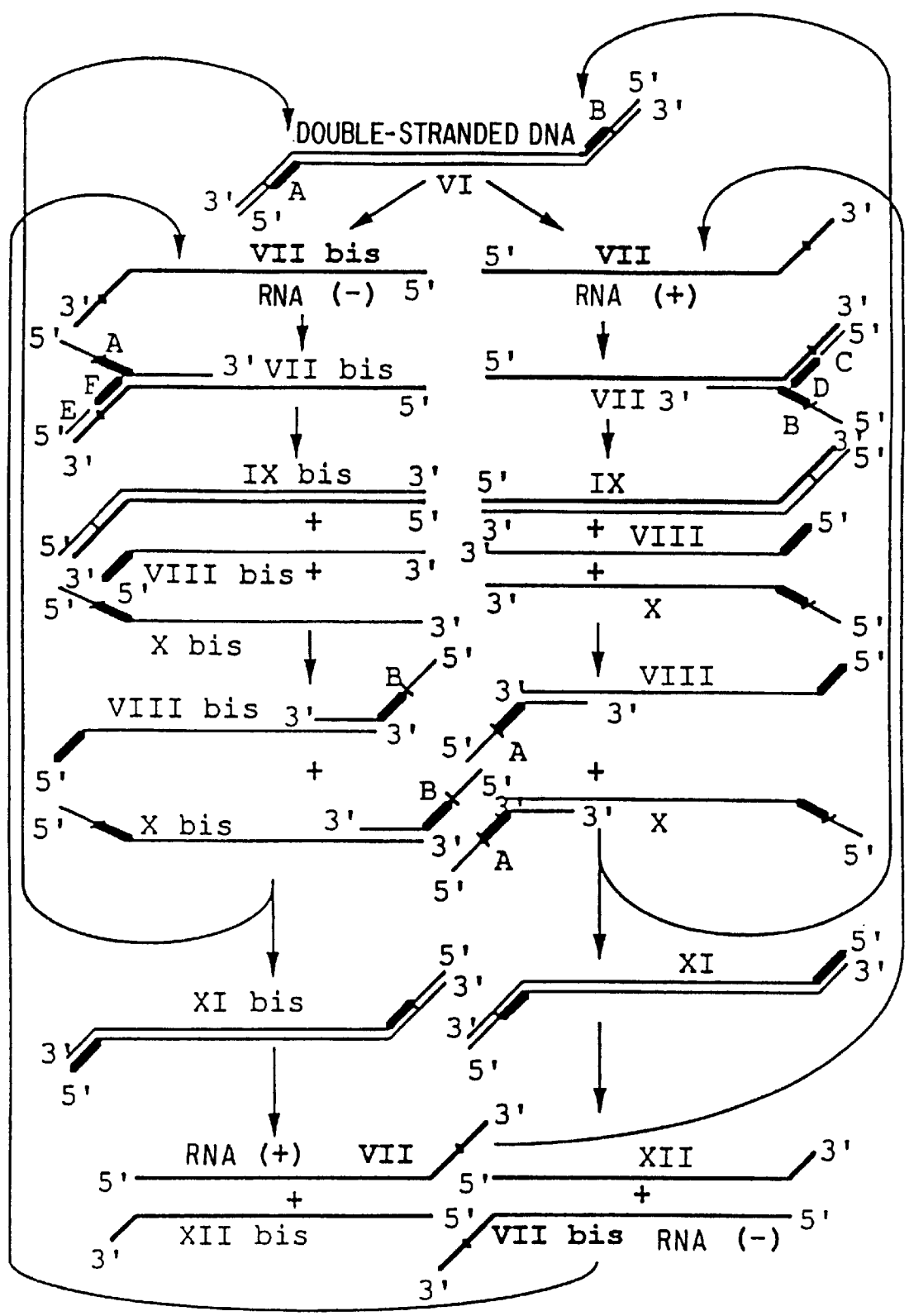
Figure 14:
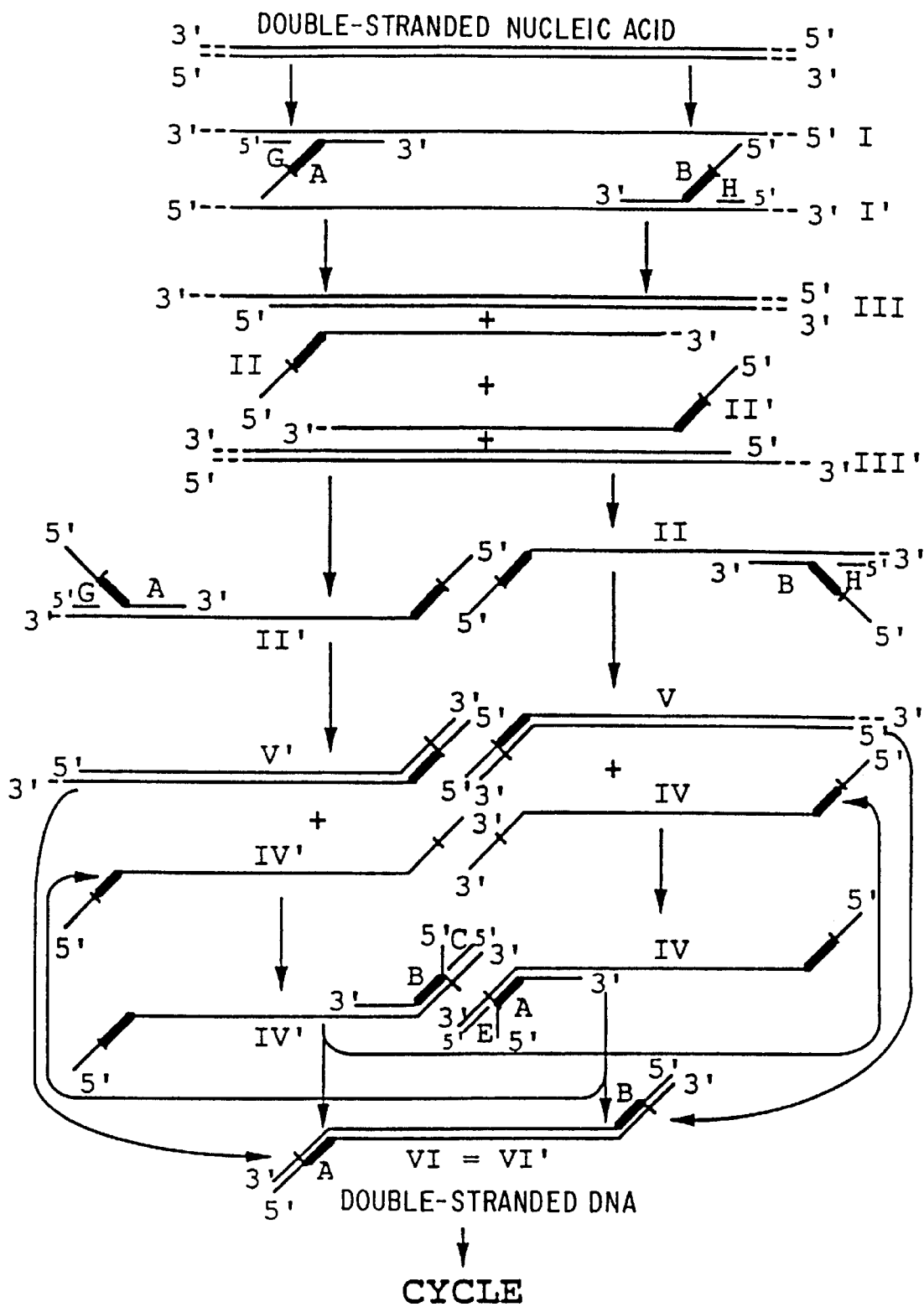
FIGS. 14 and 15 represent a simplified variant of the amplification method described in FIGS. 3 and 5 respectively, namely that the promoter primer(s) D and/or F (optional) is removed from the reaction medium.

The feasibility of the amplification method described in the present invention also depends on the capacity of RNA polymerases to transcribe complementary RNAs from one and the same double-stranded template containing functional RNA polymerase promoters at each of its ends, in particular in the method described in FIGS. 3 and 5. In order to validate this hypothesis, a double-stranded DNA template was synthesized by PCR, in the presence of primers DTA1 (SEQ ID No: 8) and DTA2 (SEQ ID No: 9), from the target pBR322. The 275 base pair fragment thus obtained is purified. It contains a portion of the sequence of the tem gene (from nucleotide 312 to 486 inclusive of SEQ ID No: 1), flanked by two promoters for T7 phage RNA polymerase, orientated for the transcription of either of the strands of the tem sequence. Each promoter sense sequence is preceded in 5' by a sequence corresponding to primer F220 (SEQ ID No: 10). The transcription of such a fragment from each of the promoters situated at its ends should theoretically result in the synthesis of two RNA populations complementary to each other and containing at their 3' end the antisense sequence of the T7 promoter (that is to say the sequence complementary to the sense sequence of the T7 promoter) followed by the sequence complementary to the oligonucleotide F220 (SEQ ID No: 10). The size of the expected RNAs is 231 bases, and they contain the sequence between nucleotides 312 and 486 (inclusive) of the tem gene (SEQ ID No: 1), or the sequence complementary to the latter. Transcription tests are carried out, using the PCR fragment containing a promoter at each end, in the 1× buffer described by Milligan et al. (1987. *Nucl. Acids Res.* 15:8783–8798), in a final volume of 50 $\mu$l, in the presence of ATP, CTP, GTP and UTP (4 mM each), of 1 U/$\mu$l of T7 phage RNA polymerase (New England Biolabs) and 1 U/$\mu$l of RNAguard (Pharmacia). The PCR template is used at $10^{11}$ copies per test and the glycerol concentration due to addition of the enzymes is 5%. The transcription is carried out for 2 hours at 37° C. and stopped by freezing to −20° C. The reaction product (10 $\mu$l) is analysed by denaturing polyacrylamide gel electrophoretic separation and then transferred onto a nylon membrane, as described in Example 1. Two membranes are thus prepared in order to carry out a hybridization of probe A28 (SEQ ID No: 5) labelled in 5' with horseradish peroxidase, on the one hand, and of probe A19 (SEQ ID No: 11) also labelled in 5' with horseradish peroxidase on the other hand. Probe A19 makes it possible to detect the RNAs complementary to the tem sequence described (SEQ ID No: 1), whereas probe A28 allows the detection of the RNAs corresponding to the tem sequence described (SEQ ID No: 1). FIG. 11 illustrates the results obtained during these tests. Probes A28 and A19 make it possible to detect $10^{12}$ copies of double stranded target DNA template of 275 base pairs (lane 1), as well as RNAs of 231 bases in the case of transcriptional tests (lane 2). The detection of the expected transcripts with the aid of the two types of probes A19 (part A) and A28 (part B) show that the transcription of complementary RNAs was carried out by T7 RNA polymerase, from each promoter of the DNA template. The production of complementary RNAs from a common DNA template containing a promoter at each of its ends demonstrates that T7 RNA polymerase is capable of carrying out the polymerization of RNAs by convergent progression on the same template. The possibility of producing complementary RNAs under these conditions with the aid of RNA polymerase therefore confirms the feasibility of the amplification method of the present invention described in FIGS. 3 and 5. These results therefore confirm that the amplification cycle described in the present invention in FIGS. 3 and 5 has an exponential character, resulting in a substantial accumulation of RNA and DNA of which the sequence corresponds to the portion of the target between the promoter primers A and B (FIG. 5).

EXAMPLE 5

Figure 15:
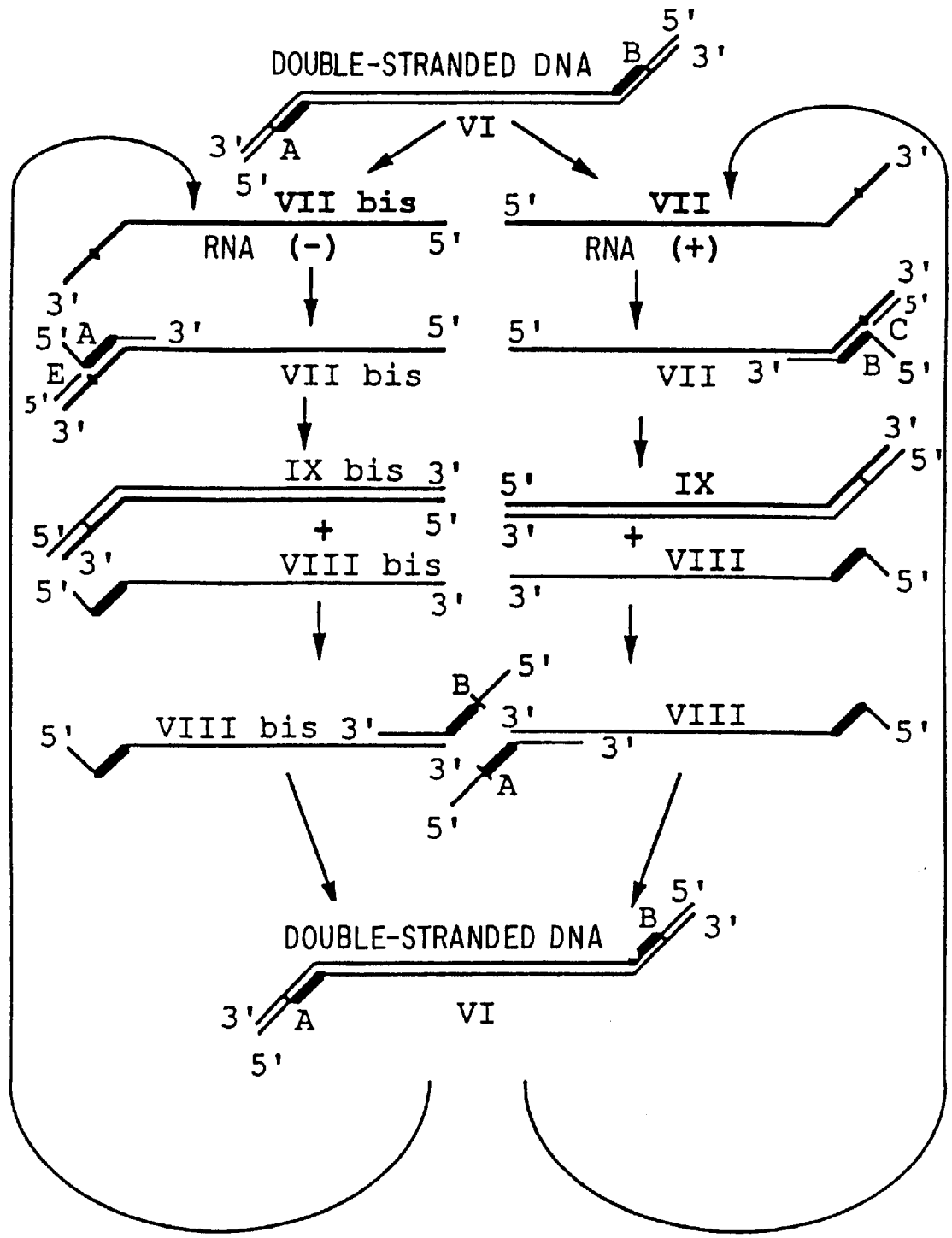
Figure 16:
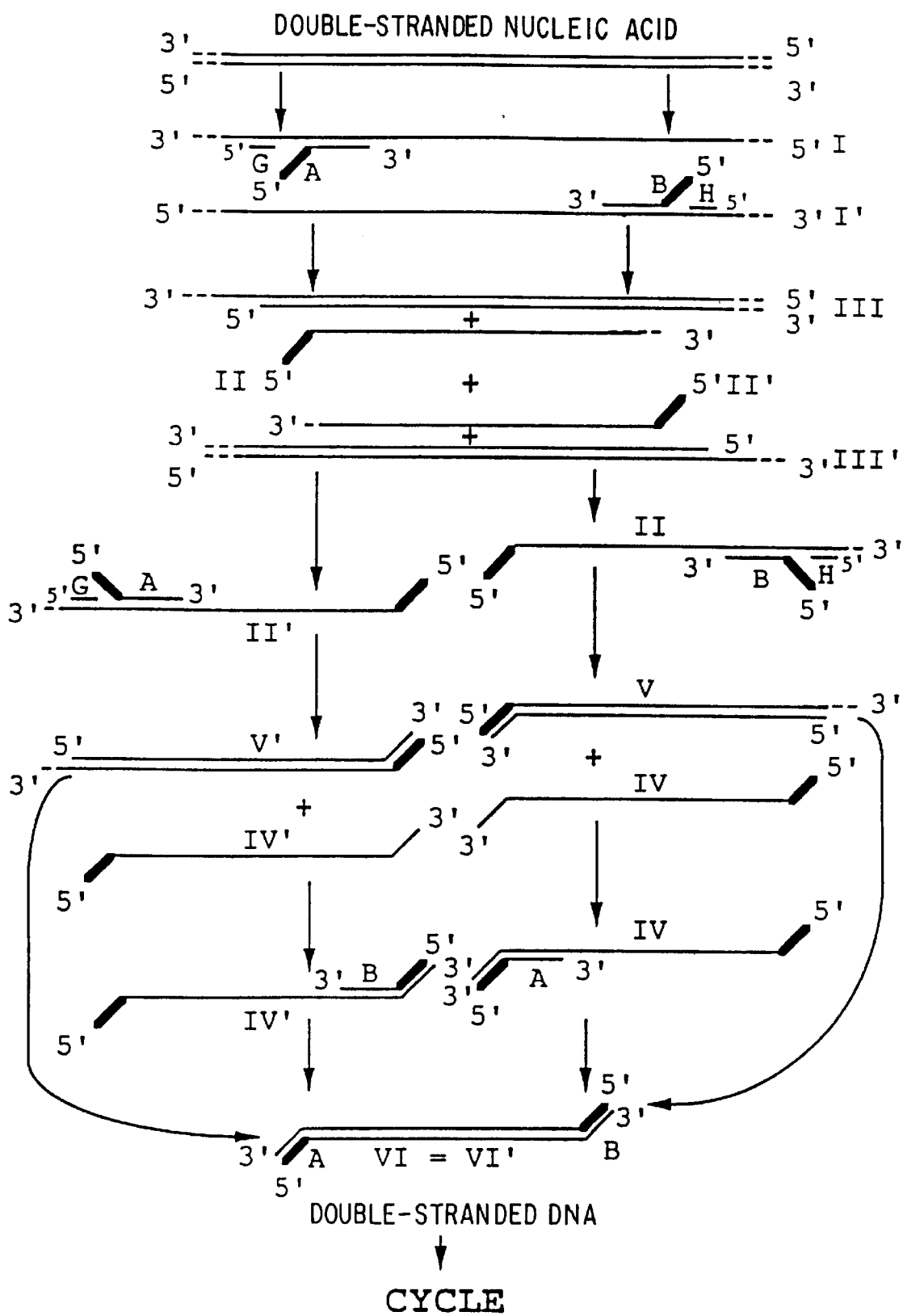
FIGS. 16 and 17 represent a simplified variant of the amplification method described in FIGS. 3 and 5 respectively, namely, primers A and B no longer contain the optional defined sequence upstream of the sense sequence of the promoter. Consequently, the use of the displacement primers C and E (FIG. 5) is no longer necessary. The role of the enzymatic displacement is provided by the sense sequences of the promoters included in A and B, that is to say primers D and F respectively.
Figure 17:
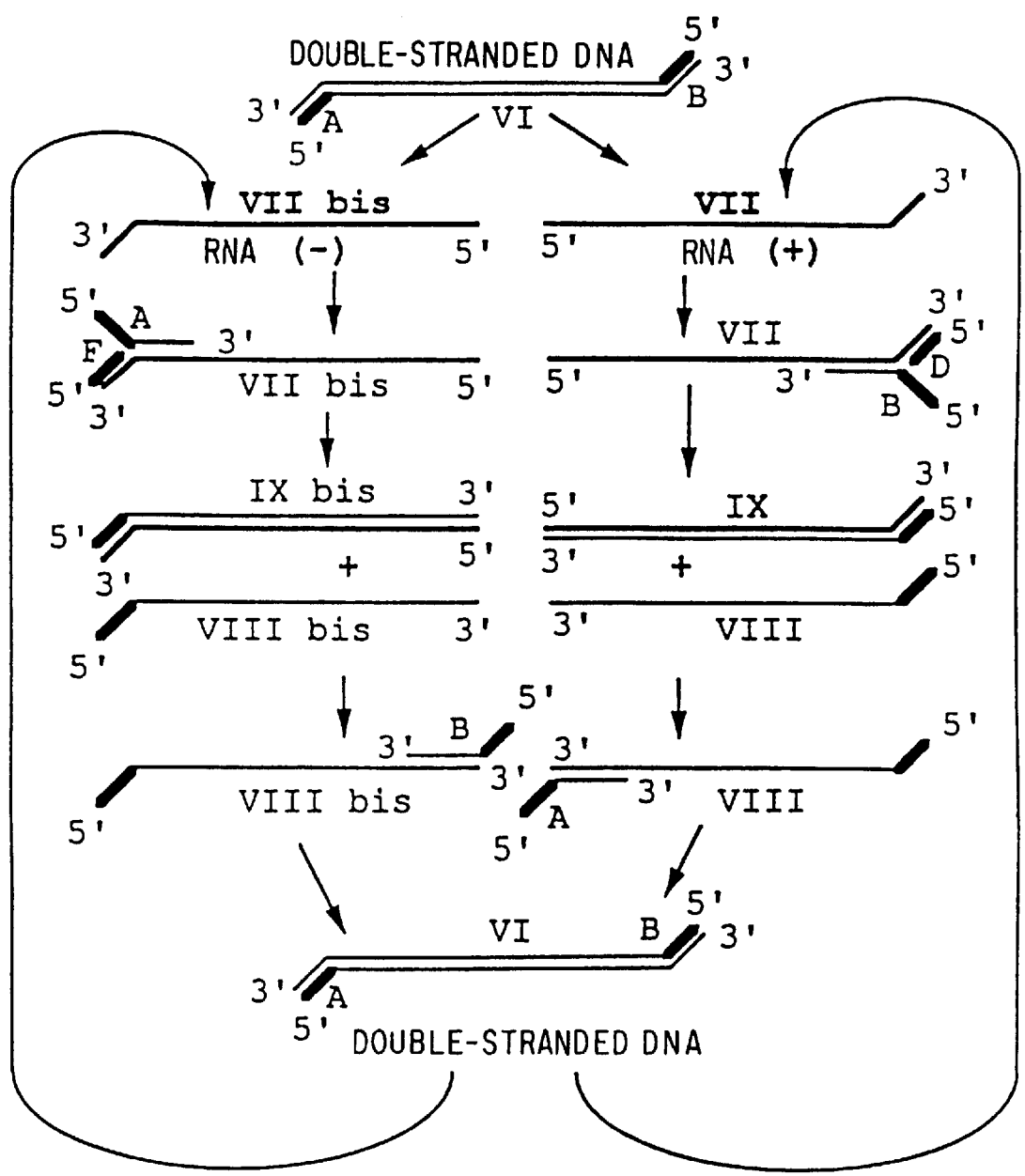
Figure 18:
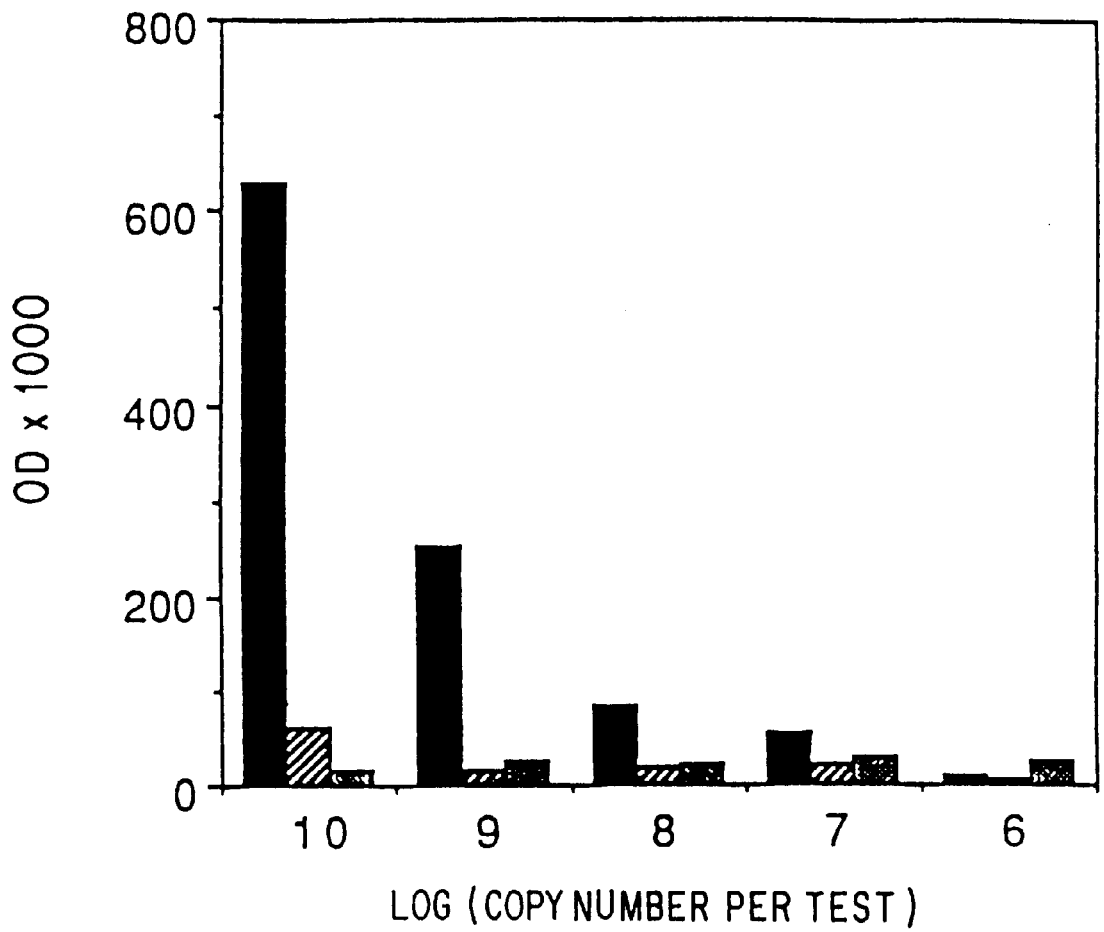
FIG. 18. A histogram showing the results of the amplification reaction described in Example 5.

The experimental validity of the DTR amplification method was proved by studying one of the amplification cycles described in the present invention, and in particular as described in FIG. 15. In order to do this, a PCR fragment of 167 base pairs was synthesized with the aid of primers DTA7 (SEQ ID No: 12) and DTA8 (SEQ ID No: 13), from pBR322, and which therefore contains a portion of the sequence of the ten gene (from nucleotide 336 to 402 inclusive of SEQ ID No: 1). This PCR fragment corresponds to one type of molecule for entry into the amplification cycle and therefore contains at each of its ends an RNA polymerase promoter sequence (in particular the T7 phage promoter), preceded in 5' by a defined sequence such as the F220 sequence (SEQ ID No: 10). In order to demonstrate the exponential character of the method, various amplification reactions were carried out in parallel in the presence of decreasing quantities of target molecule consisting of the preceding purified PCR fragment (corresponding to the entry into the amplification cycle): from $10^{10}$ to $10^6$ copies per test. The reactions were carried out in a final volume of 50 µl, in the presence of ATP, CTP, GTP and UTP (4 mM each), of dATP, dCTP, dGTP and dTTP (1 µM each) of 1 U/µl of T7. phage RNA polymerase (New England Biolabs), of 4 U/µl of MMLV reverse transcriptase "Superscript$^{II}$" (GIBCO-BRL), lacking RNase H activity, and 1 U/µl of RNAguard (Pharmacia). The reaction medium contained, in addition, the various promoter primers A and B corresponding to DTA7 and DTA8 (SEQ ID No: 12 and SEQ ID No: 13, respectively) at a concentration of 0.01 µM and the displacement primer C equivalent to E corresponding to F220 (SEQ ID No: 10) at a concentration of 1 µM. After incubating for two hours at 37° C., the amplification reactions are stopped by freezing the reaction medium to −20° C. A fraction of 5 µl, that is to say ⅒ of the reaction volume, is quantitatively analysed by capture and specific detection according to the ELOSA method (Enzyme Linked Oligo Sorbent Assay). The method involves the attachment of a capture oligonucleotide onto a solid support (microtitre plate), the denaturation of the reaction product, its hybridization with the capture probe specific for the amplified sequence and revealing by a detection probe coupled to horseradish peroxidase. The capture oligonucleotide A20 (SEQ ID No: 14) is passively attached onto the wells of a Maxisorp Nunc-Immuno plate microtitre plate according to the method already described in Patent FR 91 09057, allowing the attachment of about 5 pmol of oligonucleotide in one well. After attachment, three washes are carried out with 1× PBS-Tween buffer. The detection of the captured amplification product is carried out in accordance with the technique described earlier in Patent FR 91 09057. The 5 µl fraction to be analysed is added to a volume of 35 µl of 0.2 M sodium phosphate buffer pH 7.0, containing 1 M sodium chloride, 2 mM EDTA, 1.3% SDS, 0.24 mg/ml salmon DNA, 4% polyethylene glycol (PEG) 6000. The nucleic acids contained in this sample are denatured by addition of 5 µl of 2 M sodium hydroxide at room temperature, and neutralized after 3 minutes by addition of 5 µl of 2 M acetic acid. As control and for calibration, two RNA dilution series corresponding to the expected amplification products are prepared. The samples are then loaded into the well of a microtitre plate in which the oligonucleotide capture probe A20 (SEQ ID No: 14) has been previously attached. The amount loaded is either 50 µl of undiluted sample or the same volume of sample diluted ⅒ or ¹⁄₁₀₀. Immediately, a volume of 50 µl of 0.2 M sodium phosphate buffer pH 7.0, containing 1 M sodium chloride, 2 mM EDTA, 1.3% SDS, 0.24 mg/ml of salmon DNA, 4% polyethylene glycol (PEG) 6000 and 5 ng of detection oligonucleotide probe A18 (SEQ ID No: 15) coupled to horseradish peroxidase, is added. After incubating for 60 minutes at 37° C, the wells are washed with 1× PBS-Tween. The revealing of the peroxidase-A18 probe hybridized with the amplification product is carried out by addition of 100 µl of a solution containing the substrate ortho-phenylenediamine (OPD). The calorimetric reaction is stopped after 20 minutes by addition of 100 µl of 1 M sulphuric acid. The optical density at 492 nm is read using an AXIA microreader (BioMérieux). The results obtained are represented by the histograms in FIG. 18. For each of the target dilutions, three tests were carried out: complete test (as described above), test without displacement primer F220 (SEQ ID No: 10) and test without MMLV reverse transcriptase "Superscript$^{II}$". The results show that the amplification method (complete system) makes it possible to detect under these conditions a significant specific signal down to an initial target quantity of $10^7$ copies per test, that is to say a sensitivity of $10^6$ copies, since a fraction equivalent to ⅒th of the reaction medium is analysed under these conditions. This sensitivity is only relative and can be greatly increased if a revealing system other than colorimetry is used (for example fluorescence, chemiluminescence or bioluminescence). The results show in particular that in the absence of displacement primer F220, a specific signal is obtained only for a target quantity equal to $10^{10}$ copies per test. The difference in detection sensitivity between "with" and "without" displacement primer is therefore a factor of $10^3$, or of 3 Log of base 10 units. This demonstrates that the method allows a substantial accumulation of the amplification product, and this can only be obtained by carrying out the amplification cycle. This cycling is therefore only possible because of the presence of a displacement primer such as primer F220. Likewise, if the MMLV reverse transcriptase "Superscript$^{II}$" is suppressed, a detection signal is only obtained for an initial target quantity greater than or equal to $10^{10}$ copies per test. These latter reaction conditions in fact correspond to a transcription stage carried out on the bifunctional molecule corresponding to the entry into the amplification cycle, as described in Example 4. These data therefore show that the method is vastly more sensitive than transcription alone and that this sensitivity depends on the cycling of the method up to the transcription stage using an enzymatic displacement stage, in particular with the aid of a displacement primer in the presence of a DNA polymerase such as a reverse transcriptase. Qualitative analysis of the amplification tests by electrophoretic separation, transfer onto a nylon membrane and hybridization, as described in Example 1, with the aid of probe A28 (SEQ ID No: 5) on the one hand and of probe A18 (SEQ ID No: 15) on the other hand, coupled to horseradish peroxidase, made it possible to detect two complementary RNA molecules of 120 bases, corresponding to the expected amplification product (117 bases).

In the same manner, if the preceding amplification tests are carried out in a medium containing, in accordance with FIG. 5, in addition to the first displacement primer C (equivalent to E, in this particular case) corresponding to F220 (SEQ ID No: 10), a second displacement primer D (equivalent to F) corresponding to T7pro (SEQ ID No: 16), results and a sensitivity which are similar to those obtained with only one type of displacement primer are obtained. This shows that the technique can be simplified and is sufficiently evolutive to be adapted according to the specific cases linked to the nature of the nucleic target to be amplified.

The detection threshold of the colorimetric detection method used in this example, greater than or equal to $10^{10}$ copies per test, therefore makes it possible to deduce an amplification factor greater than or equal to $10^4$ in two hours of reaction.

EXAMPLE 6

Figure 19:
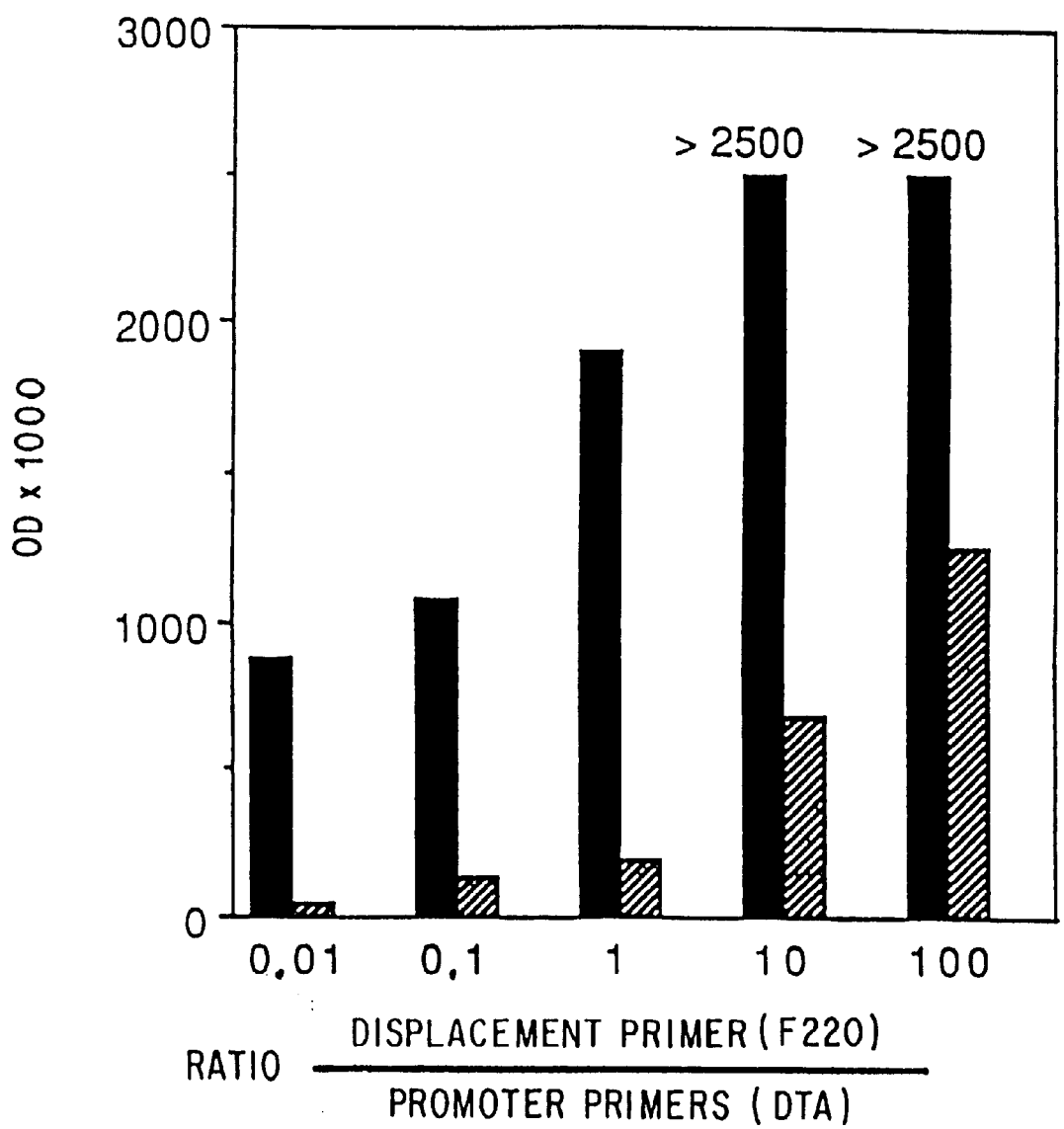
FIG. 19. A histogram showing the quantitative analysis of the amplification reaction from Example 5 using a capture probe from of SEQ ID NO 17 and a detection probe of SEQ ID NO 5. See Example 6.

The "DTR" amplification method described in the present invention is based on an exponential cycle using, in a combined manner, transcription and strand displacement. In particular, the enzymatic strand displacement calls into play, as described in FIG. 15, a reverse transcriptase, a displacement primer C (equivalent to E in this example) and two promoter primers (A and B) which are to be displaced. Within the amplification cycle, the displacement primer/displaced primer (promoter primer here) ratio greatly influences the amplification yield of the method. If the amplification is carried out under the preceding reaction conditions, in the presence of $10^8$ or $10^9$ copies of initial target, with a fixed concentration of promoter primers A and B corresponding to DTA7 (SEQ ID No: 12) and DTA8 (SEQ ID No: 13) equal to 0.1 μM, and a concentration of displacement primer C corresponding to F220 (SEQ ID No: 10) equal to 0.001, 0.01, 0.1, 1 or 10 μM, an amplification yield is obtained which increases with the displacement primer/displaced primer ratio (FIG. 19). Quantitative analysis on a microtitre plate, as described in Example 5, using a capture probe A25 (SEQ ID No: 17) and a detection probe A28 (SEQ ID No: 5), shows (FIG. 19) that the displacement primer/displaced primer ratio equal to 100 is the most favourable in this case (it will be noted that a value equal to 2500 corresponds to an optical saturation of the apparatus and therefore corresponds to a signal greater than or equal to 2500). This ratio should be adjusted according to the length of the displacement or promoter primers used, or according to the nature of the target sequence, in order to promote the cycling stage by enzymatic strand displacement.

EXAMPLE 7

Figure 20:
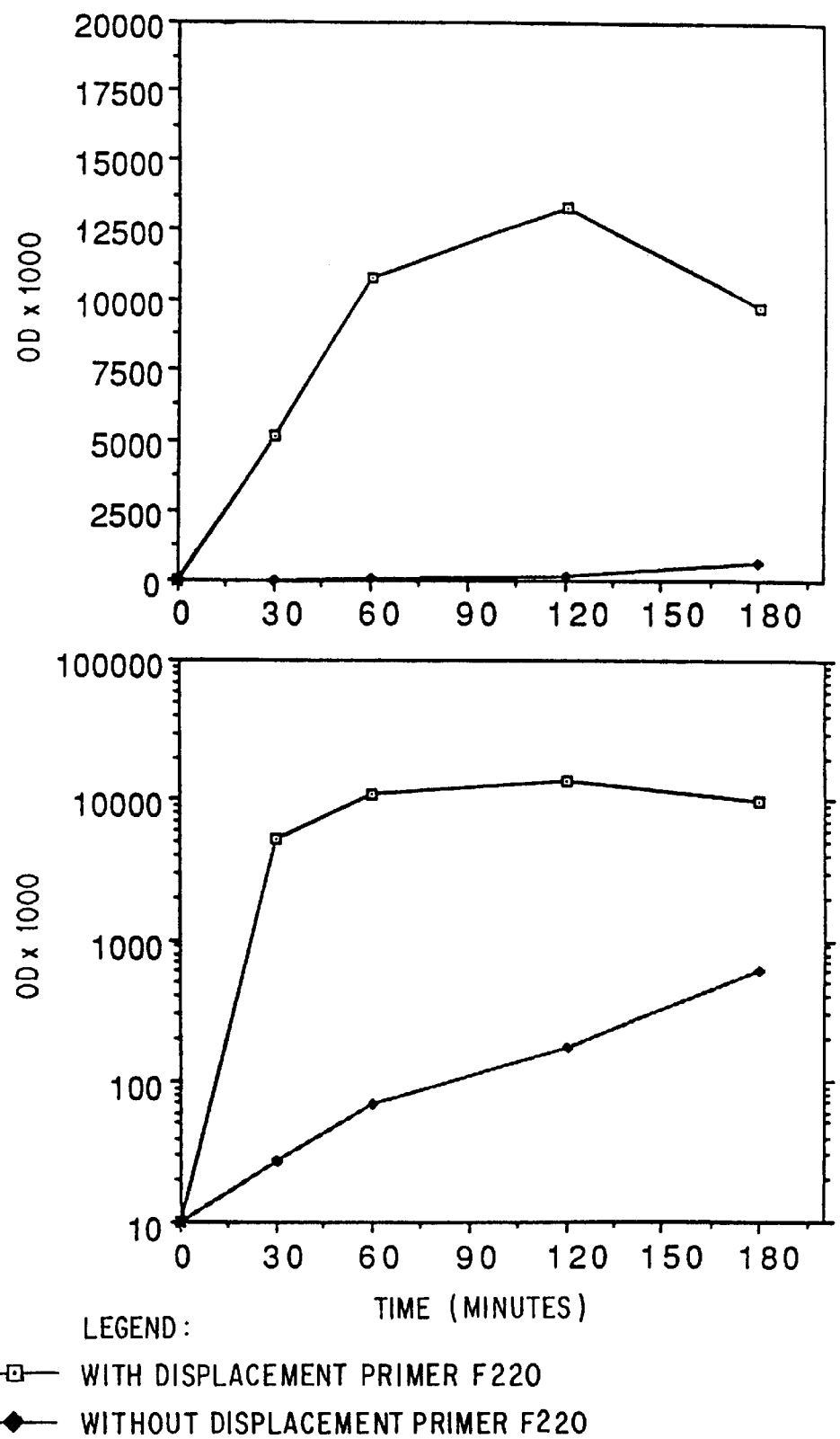
FIG. 20. A graph showing the efficiency of exponential amplification using the "DTR" technique of Example 7.

The efficiency of the exponential amplification of the "DTR" technique can be demonstrated by an analysis of the kinetics of appearance of the amplification signal. In order to do this, an amplification reaction was carried out using $10^9$ copies of target molecule, in accordance with the conditions of Example 5. At regular intervals, a 5 μl fraction of reaction mixture was collected and frozen immediately to −20° C. Quantitative analysis of the amplification signal of these fractions was carried out as described in Example 5, using a capture probe A25 (SEQ ID No: 17) and a detection probe A28 (SEQ ID No: 5). In parallel, an amplification test was carried out in the absence of displacement primer F220. The results indicated by the curves of FIG. 20 show clearly that the appearance of the signal is exponential and very rapid, since a plateau is reached from 1 hour of reaction. In parallel, the amplification reaction in the absence of displacement primer, therefore corresponding to a simple transcription reaction, results in a linear increase in the signal. The "DTR" amplification method, as opposed to transcription alone, is therefore a method resulting in the rapid and exponential accumulation of a product from an initial target sequence.

EXAMPLE 8

Figure 21:
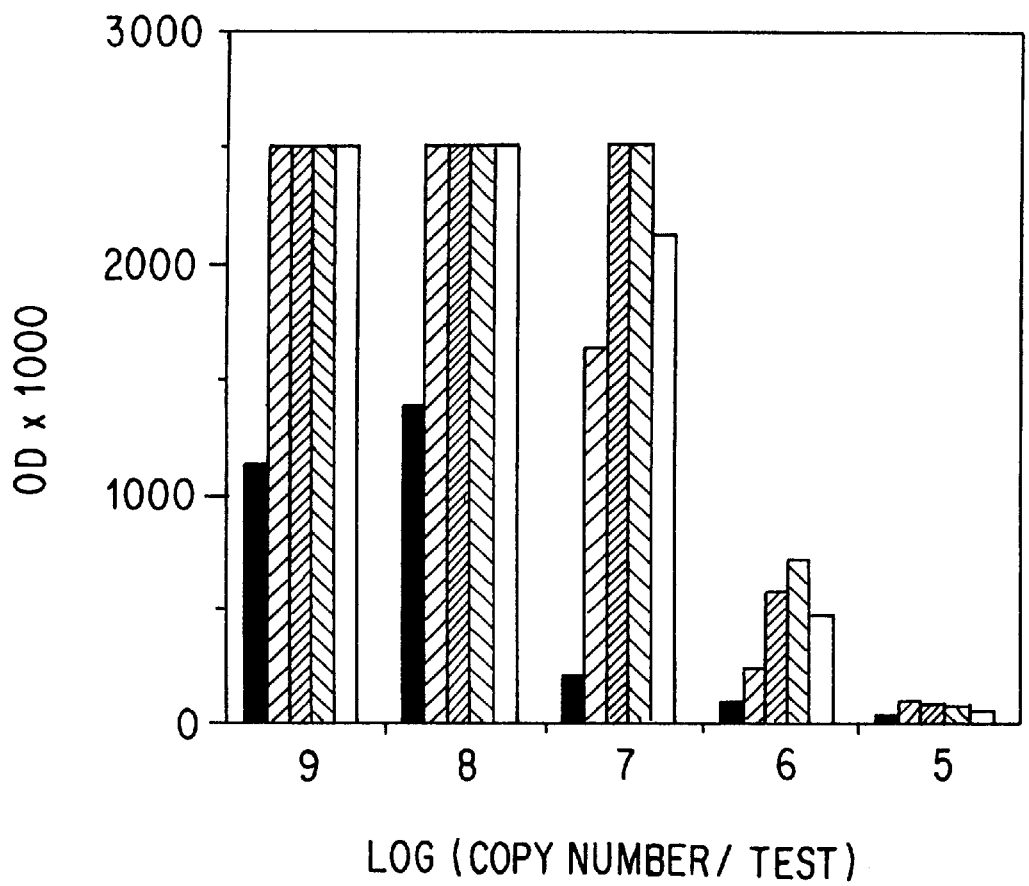
FIG. 21. A histogram showing the effect of using two types of promoters in the amplification reaction of Example 8.

The "DTR" amplification method of the present invention results essentially in a double-stranded RNA corresponding to a portion of the target sequence. In order to facilitate the detection of this double-stranded RNA by hybridization methods, or in special cases of production of single-stranded RNA, it may be useful to favour the appearance of an RNA strand at the expense of its complementary. This can be carried out by the combined use of two types of promoter primers A and B comprising a different promoter for phage (for example T7 and T3) RNA polymerase, in the presence of unbalanced RNA polymerase concentrations. For example, we synthesized by PCR, a double-stranded DNA molecule of 167 base pairs corresponding to the entry into one of the amplification cycles of the present invention (FIG. 15) using primer DTA8 (SEQ ID No: 13) comprising a T7 promoter and DTA9 (SEQ ID No: 18) containing a T3 promoter. Amplification tests were carried out on dilutions of this target in accordance with Example 5, in the presence of T7 RNA polymerase concentrations ranging from 0 to 50 U/test and a constant T3 RNA polymerase concentration equal to 50 U/test. FIG. 21 shows that the use of the enzyme ratio 6.25 U of T7 RNA polymerase to 50 U of T3 RNA polymerase makes it possible to obtain, by capture and detection with the aid of probes A25 (SEQ ID No: 17) and A28 (SEQ ID No: 5) respectively, an increased amplification signal and results in a significant signal down to a target quantity of $10^5$ copies per test, which corresponds to a sensitivity of $10^4$ copies of target molecules, by colorimetric revealing. The multiplication factor for the target amplification method, knowing that the sensitivity of the detection method is $10^{10}$ copies, is therefore $10^5$; thereby conferring on the method an efficiency which makes it useful in numerous applications.

What is claimed is:

1. A process for generating a double-stranded polynucleotide containing a sequence complementary to a sequence of interest and a single-stranded polynucleotide containing a sequence complementary to said sequence of interest, said process comprising:

obtaining a single-stranded nucleic acid comprising said sequence of interest; and contacting said single-stranded nucleic acid with a first primer and a second primer, wherein said first primer hybridizes to a first sequence of said single-stranded nucleic acid and said second primer hybridizes to a second sequence of said single-stranded nucleic acid, said second sequence overlapping with said first sequence, and said first and second sequences being located 3' to said sequence of interest, and wherein said contacting occurs in the presence of a polymerase activity allowing extension of a primer with displacement, under conditions allowing hybridization and extension of both primers, whereby an extension product of one of the primers displaces an extension product of the other primer, thus obtaining a double-stranded polynucleotide containing a sequence complementary to said sequence of interest and a displaced single-stranded polynucleotide containing a sequence complementary to said sequence of interest.

2. The process of claim 1, wherein one of said first and second primers is present in molar excess relative to the other said primer.

3. The process of claim 1, wherein said single-stranded nucleic acid is DNA.

4. The process of claim 1, wherein said single-stranded nucleic acid is RNA.

* * * * *